(12) United States Patent
Tegley

(10) Patent No.: US 7,390,820 B2
(45) Date of Patent: Jun. 24, 2008

(54) SUBSTITUTED QUINOLINONE DERIVATIVES AND METHODS OF USE

(75) Inventor: Christopher Tegley, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 494 days.

(21) Appl. No.: 10/926,218

(22) Filed: Aug. 24, 2004

(65) Prior Publication Data

US 2005/0049253 A1  Mar. 3, 2005

Related U.S. Application Data

(60) Provisional application No. 60/497,877, filed on Aug. 25, 2003.

(51) Int. Cl.
*C07D 217/22* (2006.01)
*A61K 31/4704* (2006.01)

(52) U.S. Cl. ...................................... 514/309; 546/141

(58) Field of Classification Search ................. 546/141; 514/309

See application file for complete search history.

(56) References Cited

U.S. PATENT DOCUMENTS 2,874,156 A    2/1959   Ruschig et al.

FOREIGN PATENT DOCUMENTS

| DE | 1 029 379 | | 7/1955 |
| DE | 956044 | | 1/1957 |
| WO | WO 97/08164 | * | 3/1997 |
| WO | WO 02/068406 | | 9/2002 |

OTHER PUBLICATIONS

Wang et al, Tetrahedron Letters, 1998, vol. 39, pp. 6609-6612.*
Breier et al., "The role of vascular endothelial growth factor in blood vessel formation", Trends in Cell Biology, 6:454-456 (1996).
Connell et al., "Patent focus on cancer chemotherapeutics. II Angiogenesis agents: Apr. 2000-Sep. 2000", Expert Opinion in Therapeutic Patent, 11(1):77-114 (2001).

* cited by examiner

*Primary Examiner*—Zinna N Davis
(74) *Attorney, Agent, or Firm*—Joseph W. Bulock; Ronald S. Hermenau

(57) ABSTRACT

Selected compounds are effective for prophylaxis and treatment of diseases, such as angiogenesis mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

39 Claims, No Drawings

SUBSTITUTED QUINOLINONE DERIVATIVES AND METHODS OF USE

This application claims the benefit of U.S. Provisional Application No. 60/497,877 filed Aug. 25, 2003, which is hereby incorporated by reference.

FIELD OF THE INVENTION

This invention is in the field of pharmaceutical agents and specifically relates to compounds, compositions, uses and methods for treating cancer and angiogenesis-related disorders.

BACKGROUND OF THE INVENTION

Protein kinases represent a large family of proteins which play a central role in the regulation of a wide variety of cellular processes, maintaining control over cellular function. A partial list of such kinases includes ab1, Akt, bcr-ab1, Blk, Brk, Btk, c-kit, c-met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor"(VEGF; originally termed "Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembraneous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

U.S. Pat. No. 2,874,156 describes substituted 2,3-diphenyl-1,4-dioxo-tetrahydrophthalazines. German Patent No. 1029379 describes substituted 2,3-diphenyl-1,4-dioxo-tetrahydrophthalazines. German Patent No. 956044 describes tetrahydro-phthalazines.

Compounds of the current invention have not been described as inhibitors of angiogenesis such as for the treatment of cancer.

DESCRIPTION OF THE INVENTION

A class of compounds useful in treating cancer and angiogenesis is defined by Formula I

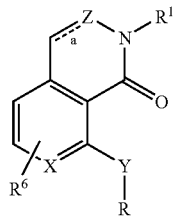

I wherein bond a is either a single bond or a double bond;
wherein X is CH or N;
wherein Y is selected from $C_{1-3}$-alkyl, $C_{2-3}$-alkenyl, O, $S(O)_n$, and $NR^4$;
wherein Z is N or $CR^5$ if bond a is a double bond;
wherein Z is C=O, $CHR^5$ or $NR^{5a}$ if bond a is a single bond;
wherein R is selected from
  a) substituted or unsubstituted 6-10 membered aryl,
  b) substituted or unsubstituted 4-6 membered heterocyclyl,
  c) substituted or unsubstituted 9-14 membered fused heterocyclyl,
  d) substituted or unsubstituted aryl-$C_{1-2}$-alkyl,
  e) substituted or unsubstituted heterocyclyl-$C_{1-2}$-alkyl, and
  f) lower alkyl;
  where substituted R is substituted with one or more substituents selected from halo, $-OR^3$, $-SR^3-SO_2R^3$, $-CO_2R^3$, $-C(O)NR^3R^3$, $-C(O)R^3$, $-NR^3R^3$, $-SO_2NR^3R^3$, $-NR^3C(O)OR^3$, $-NR^3C(O)R^3$, optionally substituted 3-6 membered heterocyclyl, optionally substituted phenyl, alkylaminoalkoxyalkoxy, nitro, cyano, oxo, lower alkyl substituted with one or more $R^2$;
wherein $R^1$ is selected from unsubstituted or substituted
  a) 6-10 membered aryl,
  b) 5-6 membered heterocyclyl,
  c) 9-14 membered fused heterocyclyl,
  d) cycloalkyl,
  e) cycloalkenyl,
  f) lower alkyl, and
  g) lower alkenyl,
  wherein substituted $R^1$ is substituted with one or more substituents independently selected from halo, $-OR^3$, $-SR^3$, $-CO_2R^3$, $-C(O)NR^3R^3$, $-C(O)R^3-NR^3R^3$, oxo, $-OC(O)R^3$, $-SO_2R^3$, $-SO_2NR^3R^3$, $-NR^3C(O)R^3$, $-NR^3C(O)R^3$, $-NR^3C(O)NR^3R^3$, optionally substituted cycloalkyl, optionally substituted 4-6 membered heterocyclyl, optionally substituted phenyl, cyano, aminoalkylcarbonylamino, alkylaminoalkylcarbonylamino, alkylaminoalkoxy, alkylaminoalkoxyalkoxy, nitro, and lower alkyl substituted with one or more $R^2$;
wherein $R^2$ is selected from H, halo, $-OR^3$, amino, $C_{1-3}$-alkylamino, $C_{1-3}$-dialkylamino, $C_{1-3}$-alkyl, optionally substituted phenyl, optionally substituted phenyl-$C_{1-3}$-alkyl, 4-6 membered heterocyclyl, and optionally substituted 4-6 membered heterocyclyl-$C_1$ $C_3$-alkyl;
wherein $R^3$ is independently selected from H, lower alkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl and lower haloalkyl;
wherein $R^4$ is independently selected from H, and lower alkyl;
wherein $R^5$ is independently selected from H, $-OR^3$, and lower alkyl;
wherein $R^{5a}$ is independently selected from H, and lower alkyl; and
wherein $R^6$ is selected from H, halo, $-OR^3$, $-SR^3$, $-CO_2R^3$, $-SR^3-C(O)NR^3R^3$, $-C(O)R^3$, $-NR^3R^3$, $-SO_2R^3$, $-SO_2NR^3R^3$, $-NR^3C(O)OR^3$, $-NR^3C(O)R^3$, $-NR^3C(O)NR^3R^3$, optionally substituted cycloalkyl, optionally substituted 4-6 membered heterocyclyl, optionally substituted phenyl, cyano, nitro, lower alkyl substituted with one or more $R^2$, lower alkenyl substituted with one or more $R^2$ and lower alkynyl substituted with one or more $R^2$;

and pharmaceutically acceptable derivatives thereof.

The invention also relates to compounds of Formula I wherein Y is NH; wherein X is CH; wherein X is CH; wherein Z is N if bond a is a double bond; wherein Z is $CHR^5$ if bond a is a single bond; and wherein $R^5$ is independently selected from H, $-OH$, and methyl; in conjunction with any of the above or below embodiments.

The invention also relates to compounds of Formula I wherein R is unsubstituted or substituted 9-10 membered fused nitrogen-containing heteroaryl and optionally further substituted 9-10 membered fused N-containing oxo-substituted heterocyclyl; in conjunction with any of the above or below embodiments.

The invention also relates to compounds of Formula I wherein R is selected from quinolin-4-yl, quinolin-5-yl, quinolin-6-yl, isoquinolin-5-yl, 2-oxo-1,2-dihydroquinol-7-yl, 1-oxo-2,3-dihydro-1H-isoindol-4-yl, quinazolin-6-yl, 4-oxo-3,4-dihydro-quinazolin-6-yl, indazol-5-yl, indazol-6-yl, indol-5-yl, isoindol-4-yl, benzimidazol-5-yl, 2-oxo-2,3-dihydro-1H-benzimidazol-5-yl and benzotriazol-6-yl; wherein R is optionally substituted with one or more substituents selected from chloro, fluoro, amino, hydroxy, methyl, ethyl, propyl, trifluoromethyl, 1-methylpiperidinylmethoxy, dimethylaminoethoxyethoxy, methoxy and ethoxy; and pharmaceutically acceptable derivatives thereof; in conjunction with any of the above or below embodiments.

The invention also relates to compounds of Formula I wherein R is substituted or unsubstituted 6-membered nitrogen containing heteroaryl-$C_{1-2}$-alkyl or 9-10 membered nitrogen containing fused heteroaryl-$C_{1-2}$-alkyl; wherein substituted R is substituted with one or more substituents independently selected from halo, amino, $C_{1-3}$-alkoxy, hydroxyl, $C_{1-3}$-alkyl and $C_{1-2}$-haloalkyl; and pharmaceutically acceptable derivatives thereof; in conjunction with any of the above or below embodiments.

The invention also relates to compounds of Formula I wherein R is substituted or unsubstituted selected from (3-pyridyl)-$(CH_2)_2-$, (4-pyridyl)-$CH_2-$, (4-pyrimidinyl)-$CH_2-$, (5-pyrimidinyl)-$CH_2-$, (6-pyrimidinyl)-$CH_2-$, (4-pyridazinyl)-$CH_2-$, (6-pyridazinyl)-$CH_2-$, 5-indazolyl-$CH_2-$, 4-quinolinyl-$CH_2-$, 6-quinolinyl-$CH_2-$, pyrrolo[2,3-b]pyridin-4-yl-$CH_2-$, pyrrolo[2,3-b]pyridin-5-yl-$CH_2-$, 5-isoquinolinyl-$CH_2-$ and 4-quinazolinyl-$CH_2-$; wherein R is unsubstituted or substituted with one or more substituents selected from chloro, fluoro, amino, hydroxy, methyl, ethyl, propyl, trifluoromethyl, methoxy and ethoxy; and pharmaceutically acceptable derivatives thereof; in conjunction with any of the above or below embodiments.

The invention also relates to compounds of Formula I wherein R is selected from indazol-6-yl, (3-pyridyl)-$(CH_2)_2-$, (4-pyridyl)-$CH_2-$, pyrrolo[2,3-b]pyridin-4-yl-$CH_2-$, pyrrolo[2,3-b]pyridin-5-yl-$CH_2-$, 6-quinolinyl-$CH_2-$ and 4-quinolinyl-$CH_2-$; and pharmaceutically acceptable derivatives thereof; in conjunction with any of the above or below embodiments.

The invention also relates to compounds of Formula I wherein $R^6$ is one or more substituents independently selected from H, halo, hydroxy, $C_{1-2}$-alkoxy, $C_{1-2}$-haloalkoxy, amino, $C_{1-2}$-alkylamino, optionally substituted 5-6 membered heterocyclyl-$C_{1-2}$-alkylamino, aminosulfonyl, $C_{3-6}$-cycloalkyl, optionally substituted 5-6 membered heterocyclyl, optionally substituted phenyl, $C_{1-4}$-alkyl, cyano, $C_{1-2}$-hydroxyalkyl, $C_{1-3}$-carboxyalkyl, nitro, $C_{2-3}$-alkenyl, $C_{2-3}$-alkynyl and $C_{1-2}$-haloalkyl; and pharmaceutically acceptable derivatives thereof; in conjunction with any of the above or below embodiments.

The invention also relates to compounds of Formula I wherein $R^6$ is one or more substituents independently selected from H, chloro, fluoro, bromo, hydroxy, methoxy, ethoxy, trifluoromethoxy, amino, dimethylamino, aminosulfonyl, carboxymethyl, cyclopropyl, optionally substituted phenyl, methyl, ethyl, propyl, cyano, hydroxymethyl, nitro, propenyl, propynyl, trifluoromethyl and unsubstituted or substituted heteroaryl selected from thienyl, furanyl, pyridyl, imidazolyl, and pyrazolyl; and pharmaceutically acceptable derivatives thereof; in conjunction with any of the above or below embodiments.

The invention also relates to compounds of Formula I wherein $R^6$ is H; and pharmaceutically acceptable derivatives thereof; in conjunction with any of the above or below embodiments.

The invention also relates to compounds of Formula I wherein $R^1$ is selected from unsubstituted or substituted 9-11 and 14 membered bicyclic saturated or partially saturated heterocyclyl; and pharmaceutically acceptable derivatives thereof; in conjunction with any of the above or below embodiments.

The invention also relates to compounds of Formula I wherein $R^1$ is selected from 1,2-dihydroquinolyl, 1,2,3,4-tetrahydroquinolinyl, 1,4-benzodioxanyl, 2-oxo-1,2-dihydroquinol-7-yl, 1-oxo-1,2,3,4-tetrahydro-isoquinolyl, 2,3-dihydro-1,1-dioxo-benzo[d]isothiazolyl, 2,3-dihydro-1H-indolyl, 2,3-dihydro-benzofuryl, 1,2,3,4-tetrahydro-isoquinolyl, 2,3,4,4a,9,9a-hexahydro-1H-3-aza-fluorenyl, and 5,6,7-trihydro-1,2,4-triazolo[3,4-a]isoquinolyl; where $R^1$ is unsubstituted or substituted with one or more substituents selected from bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperidin-4-ylmethoxy, piperidin-4-ylmethoxy, 1-methylpiperidin-4-yloxy, isopropoxy, methoxy and ethoxy; and pharmaceutically acceptable derivatives thereof; in conjunction with any of the above or below embodiments.

The invention also relates to compounds of Formula I wherein $R^1$ is selected from unsubstituted or substituted 5-6 and 9-10 membered bicyclic heteroaryl; and pharmaceutically acceptable derivatives thereof; in conjunction with any of the above or below embodiments optionally substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4-6 membered heterocyclyl-$C_1$-$C_4$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, $C_{1-4}$-alkylcarbonyl, $C_{1-3}$-alkylamino-$C_{1-3}$-alkylcarbonylamino, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-hydroxyalkyl,

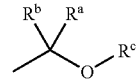

and $C_{1-4}$-alkoxy; wherein $R^c$ is selected from H, methyl, H, piperidinylethyl and methoxyethoxyethyl; and wherein $R^a$ and $R^b$ are independently selected from H and trifluoromethyl; and pharmaceutically acceptable derivatives thereof; in conjunction with any of the above or below embodiments.

The invention also relates to compounds of Formula I wherein $R^1$ is selected from thienyl, indolyl, pyridyl, 2,1,3-benzothiadiazolyl, indazolyl, quinolyl, isoquinolyl, pyrimidinyl, pyridazinyl, pyrazolyl, imidazolyl, oxazolyl, thiazolyl, thiadiazolyl, quinazolinyl, furyl and pyrrolyl; optionally substituted with one or more substituents selected from morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperidin-4-ylmethoxy, piperidin-4-ylmethoxy, 1-methylpiperidin-4-yloxy, 1,1-di(trifluoromethyl)-1-(piperidinylethoxy)methyl, 4-methylpiperazinylsulfonyl, Boc-piperidin-1-ylmethylcarbonyl, 4-methylpiperazin-1-ylcarbonylethyl, dimethylaminomethyl-carbonylamino, bromo, chloro, fluoro, iodo, nitro, amino, cyano, aminoethyl, Boc-aminoethyl, hydroxy, oxo, aminosulfonyl, cyclohexyl, phenyl, phenylmethyl, fluorosulfonyl, methylsulfonyl, methylcarbonyl, methoxycarbonyl, aminomethylcarbonyl, dimethylaminomethylcarbonyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(methoxyethoxyethoxy)methyl,
1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, isopropoxy, methoxy and ethoxy; and pharmaceutically acceptable derivatives thereof; in conjunction with any of the above or below embodiments.

The invention also relates to compounds of Formula I wherein $R^1$ is selected from phenyl optionally substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4-6 membered heterocyclyl-$C_1$-$C_4$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, $C_{1-4}$-alkylcarbonyl, $C_{1-3}$-alkylamino-$C_{1-3}$-alkylcarbonylamino, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-hydroxyalkyl,

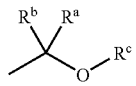

and $C_{1-4}$-alkoxy; wherein $R^c$ is selected from H, methyl, H, piperidinylethyl and methoxyethoxyethyl; and wherein $R^a$ and $R^b$ are independently selected from H and trifluoromethyl; and pharmaceutically acceptable derivatives thereof; in conjunction with any of the above or below embodiments.

The invention also relates to compounds of Formula I wherein $R^1$ is selected from phenyl optionally substituted with one or more substituents selected from morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperidin-4-ylmethoxy, piperidin-4-ylmethoxy, 1-methylpiperidin-4-yloxy, 1,1-di(trifluoromethyl)-1-(piperidinylethoxy)methyl, 4-methylpiperazinylsulfonyl, Boc-piperidin-1-ylmethylcarbonyl, 4-methylpiperazin-1-ylcarbonylethyl, dimethylaminomethyl-carbonylamino, bromo, chloro, fluoro, iodo, nitro, amino, cyano, aminoethyl, Boc-aminoethyl, hydroxy, oxo, aminosulfonyl, cyclohexyl, phenyl, phenylmethyl, fluorosulfonyl, methylsulfonyl, methylcarbonyl, methoxycarbonyl, aminomethylcarbonyl, dimethylaminomethylcarbonyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(methoxyethoxyethoxy)methyl,
1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, isopropoxy, methoxy and ethoxy; and pharmaceutically acceptable derivatives thereof; in conjunction with any of the above or below embodiments.

The invention also relates to compounds of Formula I wherein $R^1$ is

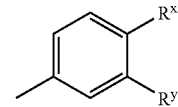

wherein each of $R^x$ and $R^y$ is independently selected from H, bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy, ethoxy, 4-methylpiperazinylsulfonyl, morpholinylmethyl, 4-methylpiperazinylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 3-dimethylaminopyrrolidin-1-ylmethyl, 1-methylpyrrolidin-2-ylmethyl, dimethylaminoethyl, dimethylaminoethoxy, piperidinylethoxy, morpholinylethyloxy, 4-methylpiperazinylethoxy, 4-isopropylpiperazinylmethoxy, piperidin-4-methoxy, 4-methylpiperidin-1-ylmethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-(N,N-dimethylamino)acetylamino and 2-(N,N-dimethylamino) ethylamino; and pharmaceutically acceptable derivatives thereof; in conjunction with any of the above or below embodiments.

The invention also relates to compounds of Formula I wherein $R^x$ is selected from chloro, tert-butyl, trifluoromethyl, pentafluoroethyl, 1,1-di(trifluoromethyl)-1-hydroxymethyl, and trifluoromethoxy; and pharmaceutically acceptable derivatives thereof; in conjunction with any of the above or below embodiments.

The invention also relates to compounds of Formula I wherein each of $R^y$ is selected from H, bromo, chloro, methyl, ethyl, trifluoromethyl, pentafluoroethyl, 1,1-di(trifluoromethyl)-1-hydroxymethyl, trifluoromethoxy, difluoromethoxy, isopropoxy, methoxy, ethoxy, 4-methylpiperazinylsulfonyl, morpholinylmethyl, 4-methylpiperazinylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 3-dimethylaminopyrrolidin-1-ylmethyl, 1-methylpyrrolidin-2-ylmethyl, dimethylaminoethyl, dimethylaminoethoxy, piperidinylethoxy, morpholinylethyloxy, 4-methylpiperazinylethoxy, 4-isopropylpiperazinylmethoxy, piperidin-4-methoxy, 4-methylpiperidin-1-ylmethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-(N,N-dimethylamino) acetylamino and 2-(N,N-dimethylamino) ethylamino; and pharmaceutically acceptable derivatives thereof; in conjunction with any of the above or below embodiments.

The invention also relates to compounds of Formula I wherein $R^1$ is selected from substituted or unsubstituted phenyl-$C_{1-2}$-alkyl; and pharmaceutically acceptable derivatives thereof; in conjunction with any of the above or below embodiments.

The invention also relates to compounds of Formula I wherein $R^1$ is selected from 3-trifluoromethylphenylmethyl, 3-trifluoromethylphenylethyl, 3-methoxyphenylmethyl, phenylethyl, 4-methoxyphenylethyl, 3,4-dimethoxyphenylethyl, 4-methylphenylethyl, 2-fluorophenylethyl, 3-fluorophenylethyl, 2-chlorophenylethyl, 4-chlorophenylethyl, 3,4-dichlorophenylethyl, and 3,5-dichlorophenylethyl; and pharmaceutically acceptable derivatives thereof; in conjunction with any of the above or below embodiments.

The invention also relates to compounds of Formula II

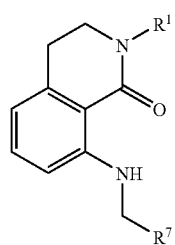

II wherein $R^1$ is selected from unsubstituted or substituted
a) 6-10 membered aryl,
b) 5-6 membered heterocyclyl,
c) 9-14 membered fused heterocyclyl, and
d) phenyl-$C_{1-3}$-alkyl,
wherein substituted $R^1$ is substituted with one or more substituents independently selected from halo, —$OR^3$, —SR, —$C_2R^3$, —$C(O)NR^3R^3$, —$C(O)R^3$, —$NR^3R^3$, oxo, —$OC(O)R^3$, —$SO_2R^3$, —$SO_2NR^3R^3$, —$NR^3C(O)$ $OR^3$, —$NR^3C(O)R^3$, —$NR^3C(O)NR^3R^3$, optionally substituted cycloalkyl, optionally substituted 4-9 membered heterocyclyl, optionally substituted phenyl, cyano, alkylaminoalkoxy, alkylaminoalkoxyalkoxy, nitro, and lower alkyl substituted with one or more $R^2$;
wherein $R^2$ is selected from H, halo, hydroxy, alkoxy, optionally substituted phenyl, optionally substituted phenyl-$C_{1-3}$- alkyl, 4-6 membered heterocyclyl, and optionally substituted 4-6 membered heterocyclyl-$C_1$-$C_3$-alkyl;
wherein $R^3$ is independently selected from H, lower alkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl and lower haloalkyl; and
wherein $R^7$ is selected from substituted or unsubstituted 6-membered and 9-10 membered heteroaryl; where substituted $R^7$ is substituted with one or more substituents selected from halo, —$OR^3$, —$SR^3$, —$SO_2R^3$, —$CO_2R^3$— $C(O)NR^3R^3$, —$C(O)R^3$, —$NR^3R^3$, —$SO_2NR^3R^3$, —$NR^3C(O)OR^3$, —$NR^3C(O)R^3$, optionally substituted 3-6 membered heterocyclyl, optionally substituted phenyl, alkylaminoalkoxyalkoxy, nitro, cyano, oxo, lower alkyl substituted with one or more $R^2$;

and pharmaceutically acceptable derivatives thereof.

The invention also relates to compounds of Formula II wherein $R^1$ is selected from phenyl substituted with one or more substituents independently selected from halo, —$OR^3$, —$SR^3$, —$CO_2R^3$—$C(O)NR^3R^3$, —$C(O)R^3$, —$NR^3R^3$, oxo, —$C(O)R^3$, —$SO_2R^3$, —$SO_2NR^3R^3$, —$NR^3C(O)OR^3$, —$NR^3C(O)R^3$, —$NR^3C(O)NR^3R^3$, optionally substituted $C_{3-6}$-cycloalkyl, optionally substituted 4-6 membered heterocyclyl, optionally substituted phenyl, cyano, $C_{1-3}$-alkylamino-$C_{1-3}$-alkoxy, $C_{1-3}$-alkylamino-$C_{1-3}$-alkoxy-$C_{1-3}$-alkoxy, nitro, and lower alkyl substituted with one or more $R^2$;
wherein $R^2$ is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and
wherein $R^3$ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-1-yl, piperidin-4-yl and piperazin-4-yl; and pharmaceutically acceptable derivatives thereof; in conjunction with any of the above or below embodiments.

The invention also relates to compounds of Formula II wherein $R^1$ is selected from phenyl substituted with 1-3 substituents independently selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; and pharmaceutically acceptable derivatives thereof; in conjunction with any of the above or below embodiments.

The invention also relates to compounds of Formula II wherein $R^1$ is selected from substituted or unsubstituted 5-6 membered or 9-10 membered fused partially unsaturated heterocyclyl or heteroaryl; wherein substituted $R^1$ is substituted with one or more substituents independently selected from halo, —$OR^3$, —$SR^3$, —$CO_2R^3$, —$C(O)NR^3R^3$, —$C(O)R^3$, —NR³R³, oxo, —OC(O)R³, —SO₂R³, —SO₂NR³R³, —NR³C(O)OR³, —NR³C(O)R³, —NR³C(O)NR³R³, optionally substituted $C_{3-6}$-cycloalkyl, optionally substituted 4-6 membered heterocyclyl, optionally substituted phenyl, cyano, alkylaminoalkoxy, alkylaminoalkoxyalkoxy, nitro, and lower alkyl substituted with one or more R²;

wherein R² is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein R³ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl; and pharmaceutically acceptable derivatives thereof; in conjunction with any of the above or below embodiments.

The invention also relates to compounds of Formula II wherein R¹ is a substituted or unsubstituted ring selected from pyrazol-5-yl, 2-oxo-1,2-dihydroquinol-7-yl, 1-oxo-1,2,3,4-tetrahydro-isoquinolyl, 2,3-dihydro-1,1-dioxo-benzo[d]isothiazolyl, benzothiazolyl, 2,3-dihydro-1H-indolyl, 2,3-dihydro-benzofuryl, 1,2,3,4-tetrahydro-isoquinolyl, quinolyl, isoquinolyl, 1,2,3,4-tetrahydroquinolyl and 5,6,7-trihydro-1,2,4-triazolo[3,4-a]isoquinolyl; wherein substituted R¹ is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholinylmethyl, methylpiperazinylmethyl, isopropyl-piperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-aminoethyl, 1-(N-isopropylamino)ethyl, 2-(N-isopropylamino)ethyl, dimethylaminopropyl, dimethylaminoethoxy, 4-chlorophenoxy, phenyloxy, 1-methylpiperidin-4-yloxy, piperidin-4-yloxy, piperidinylethoxy, morpholinylethyloxy, 4-methylpiperazinylethoxy, 4-isopropylpiperazinylethoxy, piperidin-4-methoxy, 4-methylpiperidin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylamino)pyrrolidin-1-yloxy, isopropoxy, methoxy and ethoxy; and pharmaceutically acceptable derivatives thereof; in conjunction with any of the above or below embodiments.

The invention also relates to compounds of Formula II wherein R¹ is substituted with 1-3 substituents independently selected from chloro, fluoro, amino, aminoethyl, hydroxy, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, methylcarbonyl, trifluoromethoxy, 1-methylpiperidin-4-yloxy, piperidin-4-yloxy, piperidinylethoxy, morpholinylethyloxy, 4-methylpiperazinylethoxy, 4-isopropylpiperazinylethoxy, piperidin-4-methoxy, 4-methylpiperidin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylamino)pyrrolidin-1-ylethoxy, isopropoxy, methoxy and ethoxy; and pharmaceutically acceptable derivatives thereof; in conjunction with any of the above or below embodiments.

The invention also relates to compounds of Formula II wherein R¹ is selected from 3-trifluoromethylphenylmethyl, 3-trifluoromethylphenylethyl, 3-methoxyphenylmethyl, phenylethyl, 4-methoxyphenylethyl, 3,4-dimethoxyphenylethyl, 4-methylphenylethyl, 2-fluorophenylethyl, 3-fluorophenylethyl, 2-chlorophenylethyl, 4-chlorophenylethyl, 3,4-dichlorophenylethyl, and 3,5-dichlorophenylethyl; and pharmaceutically acceptable derivatives thereof; in conjunction with any of the above or below embodiments.

The invention also relates to compounds of Formula II wherein R⁷ is selected from substituted or unsubstituted 6 membered nitrogen containing heteroaryl, where substituted R⁷ is substituted with one or more substituents selected from halo, —OR³, —SR³, —SO₂R³, —CO₂R³, —C(O)NR³R³, —C(O)R³, —NR³R³, —SO₂NR³R³, —NR³C(O)OR³, —NR³C(O)R³, optionally substituted 3-6 membered heterocyclyl, optionally substituted phenyl, alkylaminoalkoxyalkoxy, nitro, cyano, oxo, lower alkyl substituted with one or more R²;

wherein R² is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein R³ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl;

and pharmaceutically acceptable derivatives thereof; in conjunction with any of the above or below embodiments.

The invention also relates to compounds of Formula II wherein R⁷ is selected from 4-pyridyl, 4-pyrimidinyl, 5-pyrimidinyl, 6-pyrimidinyl, 4-pyridazinyl and 6-pyridazinyl; and pharmaceutically acceptable derivatives thereof; in conjunction with any of the above or below embodiments.

The invention also relates to compounds of Formula II wherein R⁷ is selected from substituted or unsubstituted 9-10 membered nitrogen containing heteroaryl, where substituted R⁷ is substituted with one or more substituents selected from halo, —OR³, —SR³, —SO₂R³, —CO₂R³, —C(O)NR³R³, —C(O)R³, —NR³R³, —SO₂NR³R³, —NR³C(O)OR³, —NR³C(O)R³, Boc, optionally substituted 3-9 membered heterocyclyl, optionally substituted phenyl, alkylaminoalkoxyalkoxy, nitro, cyano, oxo, lower alkyl substituted with one or more R²;

wherein R² is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein R³ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl;

and pharmaceutically acceptable derivatives thereof; in conjunction with any of the above or below embodiments.

The invention also relates to compounds of Formula II wherein R⁷ is selected from 5-indazolyl, 4-quinolinyl, 6-quinolinyl, pyrrolo[2,3-b]pyridin-4-yl, pyrrolo[2,3-b]pyridin-3-yl, 5-isoquinolinyl and 4-quinazolinyl; and pharmaceutically acceptable derivatives thereof; in conjunction with any of the above or below embodiments.

The invention also relates to compounds of Formula II wherein R¹ is selected from 4-tertbutylphenyl, 3,3-dimethyl-2,3-dihydroindolyl, 1-acetyl-3,3-dimethyl-2,3-dihydroindolyl, 3-tert-butylpyrazol-5-yl, 4,4-dimethyl-1,2,3,4-tetrahydroisoquinolin-7-yl, 4,4-dimethyl-2-(3-pyrrolo[2,3-b]pyridinyl)-1,2,3,4-tetrahydroisoquinolin-7-yl, and 4,4-dimethyl-2-(Boc)-1,2,3,4-tetrahydroisoquinolin-7-yl; wherein R⁵ is H; and and wherein R⁷ is selected from 6-quinolinyl, pyrrolo[2,3-b]pyridin-3-yl, 4-pyridyl and 3-aminopyrid-4-yl; and pharmaceutically acceptable derivatives thereof; in conjunction with any of the above or below embodiments.

The invention also relates to compounds of Formula III

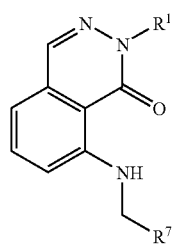

III wherein R¹ is selected from unsubstituted or substituted
a) 6-10 membered aryl,
b) 5-6 membered heterocyclyl,
c) 9-14 membered fused heterocyclyl, and
d) phenyl-$C_{1-3}$-alkyl,
wherein substituted R¹ is substituted with one or more substituents independently selected from halo, —OR³, —SR³, —CO₂R³, —C(O)NR³R³, —C(O)R³—NR³R³ oxo, —OC(O)³R³, —SO₂R³, —SO₂NR³R³, —NR³C(O)OR³, —NR³C(O)R, —NR³C(O)NR³R³, optionally substituted cycloalkyl, optionally substituted 4-9 membered heterocyclyl, optionally substituted phenyl, cyano, alkylaminoalkoxy, alkylaminoalkoxyalkoxy, nitro, and lower alkyl substituted with one or more R²;
wherein R² is selected from H, halo, hydroxy, alkoxy, optionally substituted phenyl, optionally substituted phenyl-$C_{1-3}$-alkyl, 4-6 membered heterocyclyl, and optionally substituted 4-6 membered heterocyclyl-$C_1$-$C_3$-alkyl;
wherein R³ is independently selected from H, lower alkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl and lower haloalkyl; and wherein R⁷ is selected from substituted or unsubstituted 6-membered and 9-10 membered heteroaryl; where substituted R⁷ is substituted with one or more substituents selected from halo, —OR³, —SR³, —SO₂R³, —CO₂R³, —C(O)NR³R³, —C(O)R³, —NR³R³, —SO₂NR³R³, —NR³C(O)OR³, —NR³C(O)R³, optionally substituted 3-6 membered heterocyclyl, optionally substituted phenyl, alkylaminoalkoxyalkoxy, nitro, cyano, oxo, lower alkyl substituted with one or more R²;

and pharmaceutically acceptable derivatives thereof.

The invention also relates to compounds of Formula III wherein R¹ is selected from phenyl substituted with one or more substituents independently selected from halo, —OR³, —SR³, CO₂R³, C(O)NR³R³, —C(O)R³, —NR³R³, oxo, —OC(O)R³, —SO₂R³, —SO₂NR³R³, —NR³C(O)OR³, —NR³C(O)R³, —NR³C(O)NR³R³, optionally substituted $C_{3-6}$-cycloalkyl, optionally substituted 4-6 membered heterocyclyl, optionally substituted phenyl, cyano, $C_{1-3}$-alkylamino-$C_{1-3}$-alkoxy, $C_{1-3}$-alkylamino-$C_{1-3}$-alkoxy-$C_{1-3}$-alkoxy, nitro, and lower alkyl substituted with one or more R²;
wherein R² is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein R³ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-1-yl, piperidin-4-yl and piperazin-4-yl; and pharmaceutically acceptable derivatives thereof; in conjunction with any of the above or below embodiments.

The invention also relates to compounds of Formula III wherein R¹ is selected from phenyl substituted with 1-3 substituents independently selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; and pharmaceutically acceptable derivatives thereof; in conjunction with any of the above or below embodiments.

The invention also relates to compounds of Formula III wherein R¹ is selected from substituted or unsubstituted 5-6 membered or 9-10 membered fused patially unsaturated heterocyclyl and heteroaryl; wherein substituted R¹ is substituted with one or more substituents independently selected from halo, —OR³, —SR³, —CO₂R³, —C(O)NR³R³, —C(O)R³, —NR³R³, oxo, —OC(O)R³, —SO₂R³, —SO₂NR³R³, —NR³C(O)OR³, —NR³C(O)R³, —NR³C(O)NR³R³, optionally substituted $C_{3-6}$-cycloalkyl, optionally substituted 4-6 membered heterocyclyl, optionally substituted phenyl, cyano, alkylaminoalkoxy, alkylaminoalkoxyalkoxy, nitro, and lower alkyl substituted with one or more R²; wherein R² is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein R³ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl; and pharmaceutically acceptable derivatives thereof; in conjunction with any of the above or below embodiments.

The invention also relates to compounds of Formula III wherein $R^1$ is a substituted or unsubstituted ring selected from pyrazol-5-yl, 2-oxo-1,2-dihydroquinol-7-yl, 1-oxo-1,2,3,4-tetrahydro-isoquinolyl, 2,3-dihydro-1,1-dioxo-benzo[d]isothiazolyl, 2,3-dihydro-1H-indolyl, 2,3-dihydro-benzofuryl, 1,2,3,4-tetrahydro-isoquinolyl, 1,2,3,4-tetrahydroquinolyl and 5,6,7-trihydro-1,2,4-triazolo[3,4-a]isoquinolyl; wherein substituted $R^1$ is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholinylmethyl, methylpiperazinylmethyl, isopropyl-piperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-aminoethyl, 1-(N-isopropylamino)ethyl, 2-(N-isopropylamino)ethyl, dimethylaminopropyl, dimethylaminoethoxy, 4-chlorophenoxy, phenyloxy, 1-methylpiperidin-4-yloxy, piperidin-4-yloxy, piperidinylethoxy, morpholinylethyloxy, 4-methylpiperazinylethoxy, 4-isopropylpiperazinylethoxy, piperidin-4-methoxy, 4-methylpiperidin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylamino)pyrrolidin-1-ylethoxy, isopropoxy, methoxy and ethoxy; and pharmaceutically acceptable derivatives thereof; in conjunction with any of the above or below embodiments.

The invention also relates to compounds of Formula III wherein $R^1$ is substituted with 1-3 substituents independently selected from chloro, fluoro, amino, aminoethyl, hydroxy, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, methylcarbonyl, trifluoromethoxy, 1-methylpiperidin-4-yloxy, piperidin-4-yloxy, piperidinylethoxy, morpholinylethyloxy, 4-methylpiperazinylethoxy, 4-isopropylpiperazinylethoxy, piperidin-4-methoxy, 4-methylpiperidin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylamino)pyrrolidin-1-ylethoxy, isopropoxy, methoxy and ethoxy; and pharmaceutically acceptable derivatives thereof; in conjunction with any of the above or below embodiments.

The invention also relates to compounds of Formula III wherein $R^1$ is selected from 3-trifluoromethylphenylmethyl, 3-trifluoromethylphenylethyl, 3-methoxyphenylmethyl, phenylethyl, 4-methoxyphenylethyl, 3,4-dimethoxyphenylethyl, 4-methylphenylethyl, 2-fluorophenylethyl, 3-fluorophenylethyl, 2-chlorophenylethyl, 4-chlorophenylethyl, 3,4-dichlorophenylethyl, and 3,5-dichlorophenylethyl; and pharmaceutically acceptable derivatives thereof; in conjunction with any of the above or below embodiments.

The invention also relates to compounds of Formula III wherein $R^7$ is selected from substituted or unsubstituted 6 membered nitrogen containing heteroaryl, where substituted $R^7$ is substituted with one or more substituents selected from halo, —$OR^3$, —$SR^3$, —$SO_2R^3$, —$CO_2R^3$, —$C(O)NR^3R^3$, —$C(O)R^3$, —$NR^3R^3$, —$SO_2NR^3R^3$, —$NR^3C(O)OR^3$, —$NR^3C(O)R^3$, optionally substituted 3-6 membered heterocyclyl, optionally substituted phenyl, alkylaminoalkoxyalkoxy, nitro, cyano, oxo, lower alkyl substituted with one or more $R^2$;

wherein $R^2$ is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein $R^3$ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl; and pharmaceutically acceptable derivatives thereof; in conjunction with any of the above or below embodiments.

The invention also relates to compounds of Formula III wherein $R^7$ is selected from 4-pyridyl, 4-pyrimidinyl, 5-pyrimidinyl, 6-pyrimidinyl, 4-pyridazinyl and 6-pyridazinyl; and pharmaceutically acceptable derivatives thereof; in conjunction with any of the above or below embodiments.

The invention also relates to compounds of Formula III wherein $R^7$ is selected from substituted or unsubstituted 9-10 membered nitrogen containing heteroaryl, where substituted $R^7$ is substituted with one or more substituents selected from halo, —$OR^3$, —$SR^3$, —$SO_2R^3$, —$CO_2R^3$, —$C(O)NR^3R^3$, —$C(O)R^3$—$NR^3R^3$, —$SO_2NR^3R^3$, —$NR^3C(O)OR^3$, —$NR^3C(O)R^3$, Boc, optionally substituted 3-9 membered heterocyclyl, optionally substituted phenyl, alkylaminoalkoxyalkoxy, nitro, cyano, oxo, lower alkyl substituted with one or more $R^2$;

wherein $R^2$ is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein $R^3$ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl; and pharmaceutically acceptable derivatives thereof; in conjunction with any of the above or below embodiments.

The invention also relates to compounds of Formula III wherein $R^7$ is selected from 5-indazolyl, 4-quinolinyl, 6-quinolinyl, pyrrolo[2,3-b]pyridin-4-yl, pyrrolo[2,3-b]pyridin-3-yl, 5-isoquinolinyl and 4-quinazolinyl; and pharmaceutically acceptable derivatives thereof; in conjunction with any of the above or below embodiments.

The invention also relates to compounds of Formula III wherein $R^1$ is selected from 4-tertbutylphenyl, 3,3-dimethyl-2,3-dihydroindolyl, 1-acetyl-3,3-dimethyl-2,3-dihydroindolyl, 3-tert-butylpyrazol-5-yl, 4,4-dimethyl-1,2,3,4-tetrahydroisoquinolin-7-yl, 4,4-dimethyl-2-(3-pyrrolo[2,3-b]pyridinyl)-1,2,3,4-tetrahydroisoquinolin-7-yl, and 4,4-dimethyl-2-(Boc)-1,2,3,4-tetrahydroisoquinolin-7-yl; wherein $R^5$ is H; and and wherein $R^7$ is selected from 6-quinolinyl, pyrrolo[2,3-b]pyridin-3-yl, 4-pyridyl and 3-aminopyrid-4-yl; and pharmaceutically acceptable derivatives thereof; in conjunction with any of the above or below embodiments.

A family of specific compounds of particular interest within Formula I consists of compounds and pharmaceutically-acceptable derivatives thereof as follows:

2-(4-(1,1-dimethylethyl)phenyl)-8-((4-pyridinylmethyl)amino)-1(2H)-phthalazinone;

2-(4-(1,1-dimethylethyl)phenyl)-8-((1H-pyrrolo[2,3-b]pyridin-3-ylmethyl)amino)-1(2H)-phthalazinone; and 2-(4-(1,1-dimethylethyl)phenyl)-8-((4-pyridinylmethyl)amino)-3,4-dihydro-1(2H)-isoquinolinone.

Indications

Compounds of the present invention would be useful for, but not limited to, the prevention or treatment of angiogenesis related diseases. The compounds of the invention have kinase inhibitory activity, such as VEGFR/KDR inhibitory activity. The compounds of the invention are useful in therapy as antineoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, be consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of this invention may also act as inhibitors of other protein kinases, e.g. tie-2, lck, src, fgf, cmet, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a sindle compound, salt and the like.

Definitions

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a] isoquinolyl, 3,4-dihydro-2H-benzo[1,4]oxazinyl, benzo[1,4] dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I-III" includes any sub formulas.

The compounds of the invention are endowed with kinase inhibitory activity, such as KDR inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR.

The present invention comprises a pharmaceutical composition comprising a therapeutically-effective amount of a compound of Formulas I-III in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I-III.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diazi-quone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The present invention comprises processes for the preparation of a compound of Formula I-III.

Also included in the family of compounds of Formula I-III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-III include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-III.

GENERAL SYNTHETIC PROCEDURES

The compounds of the invention can be synthesized according to the following procedures of Schemes 1-6, wherein the substituents are as defined for Formulas I-III, above, except where further noted.

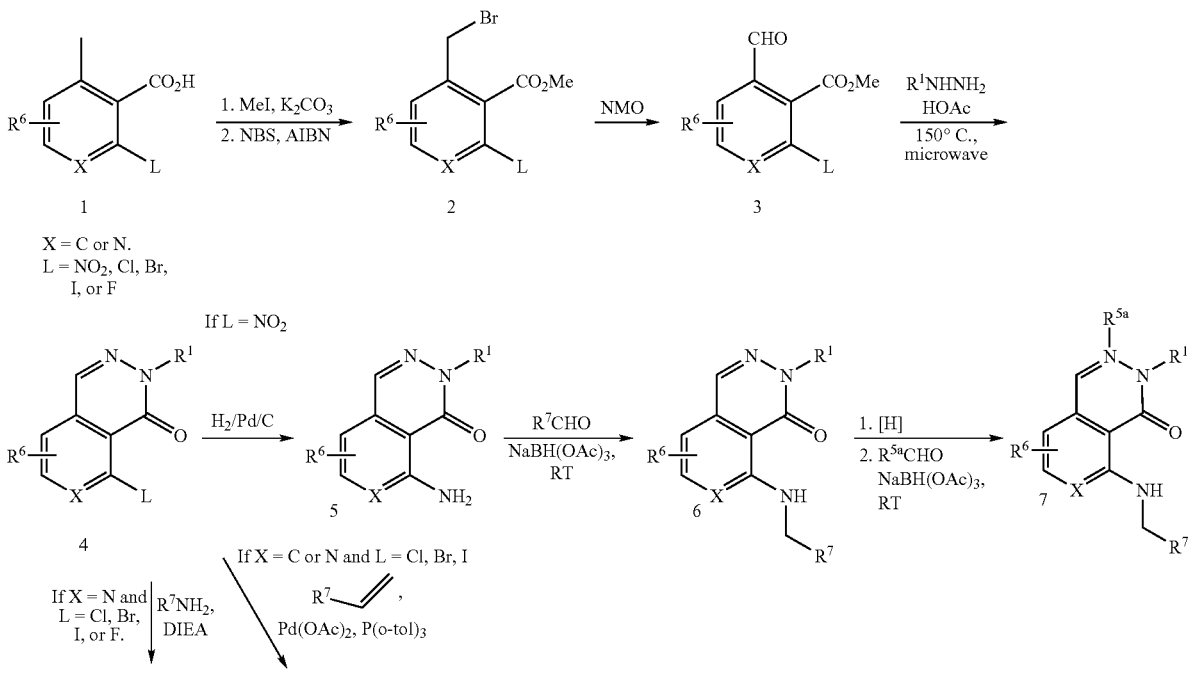

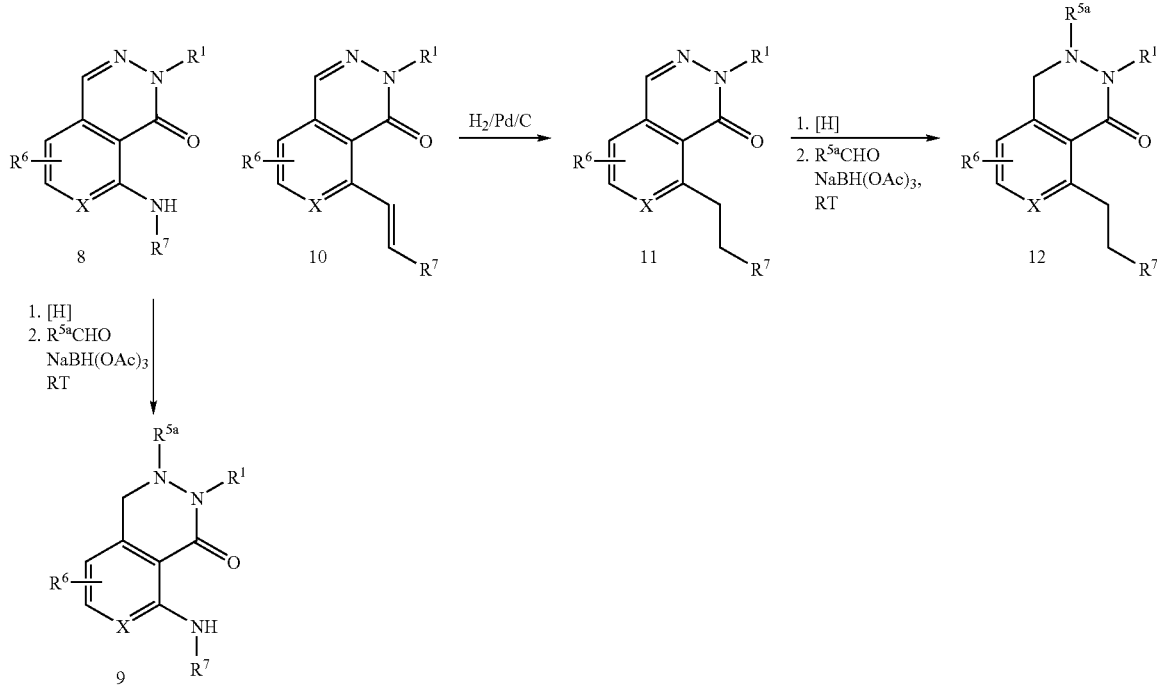

Compounds of Formula I can be prepared by the procedure wherein a 2-methyl-6-nitro-benzoic acid 1, for example, is esterified followed by benzylic bromination and oxidation to the aldehyde 3. Reaction of the aldehyde with a hydrazine followed by cyclization affords the 8-nitro-2H-phthalizin-1-one 4. The 8-nitro-2H-phthalizin-1-one 4 can be reduced under standard hydrogenation conditions and reacted with an aldehyde to afford compounds of Formula I 6. In addition, if X=N and L=halogen (Br, Cl, F, or I) then the pyridine can be reacted with an aryl or alkyl amine, for example, to give the corresponding substituted 8-amino-7-aza-2H-phthalazin-1-one 3. In addition, if X=C or N and L=halogen (Br, Cl, or I) then reaction with an olefin via a Heck reaction affords the corresponding vinyl compound 10 which can be reduced under standard hydrogenation conditions to give 11. Further, each of the 2H-phthalazin-1-one rings thus formed can be reduced under suitable reaction conditions to afford the corresponding 3,4-dihydro-2H-phthalazin-1-one ($R^{5a}$ is H) which can then be alkylated ($R^{5a}$ is lower alkyl) by reductive amination, for example to give 7, 9 and 12.

Scheme 2

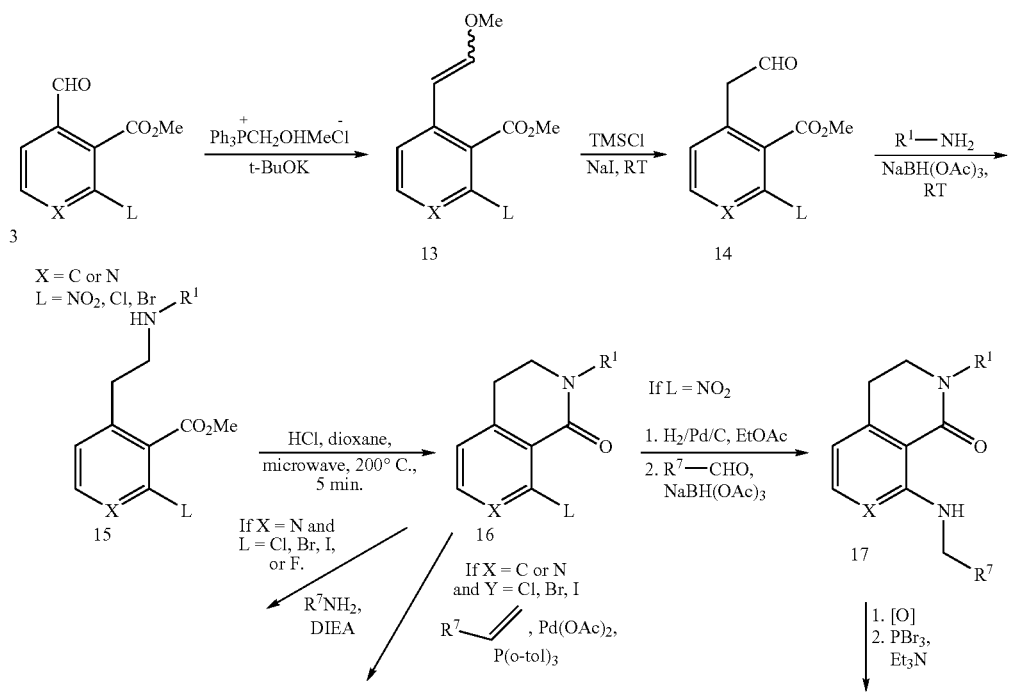

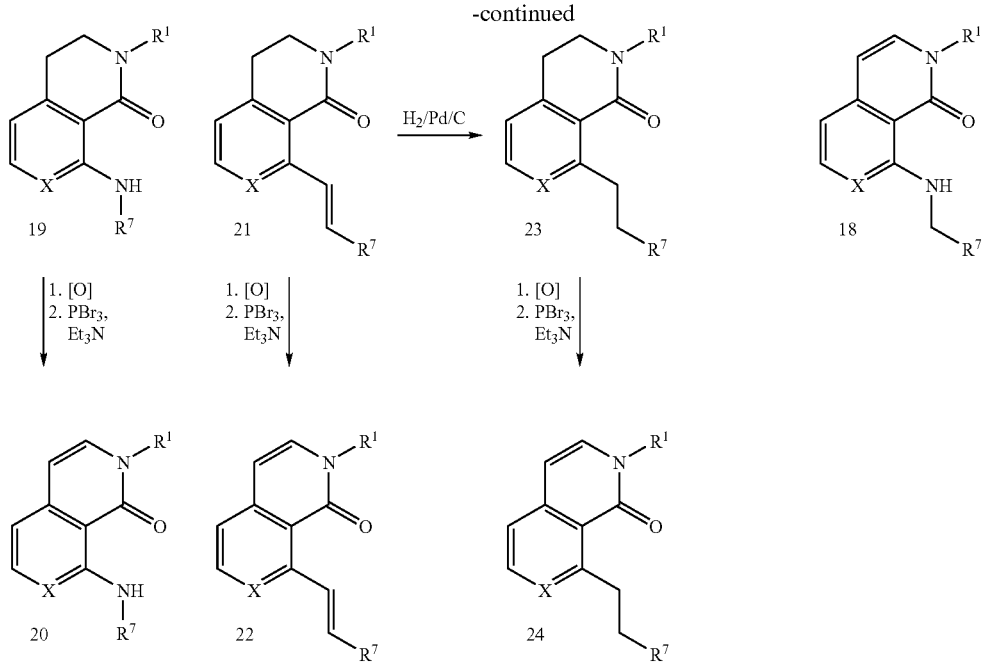

Compounds of Formula II can be prepared by the procedure wherein the same aldehyde 3 described in Scheme 1, for example, is reacted under standard Wittig conditions to give the enol-ether 13 which is then converted by known processes to the homologated aldehyde 14. Reaction of the aldehyde with an amine such as an aniline affords a phenethyl amine 15 which is then cyclized under acidic conditions to give the 8-nitro-3,4-dihydro-2H-isoquinolin-1-one 16. The 8-nitro-3,4-dihydro-2H-isoquinolin-1-one 16 can be reduced under standard hydrogenation conditions and then reacted with an aldehyde to prepare compounds of Formula II 17. Also, if X=N and L=halogen (Cl, Br, or I) then the 7-aza-isoquinolinone can either be aminated with an aryl or alkyl amine or reacted with an olefin via a Heck reaction to give respectively the corresponding substituted 8-amino-3,4-dihydro-2H-isoquinolin-1-one 19 or the vinyl compound 21 which can be reduced via standard hydrogenation conditions 23. Also, if X=C and L=halogen (Cl, Br, or I) then the 8-halo-isoquinolinone can react with an olefin via a Heck reaction to give the corresponding vinyl compound 21 which can be reduced by standard hydrogenation conditions 23. In addition, each of the 3,4-dihydro-2H-isoquinolin-1-one rings 17, 19, 21 & 23 thus formed can be converted to the corresponding 2H-isoquinolin-1-ones 18, 20, 22 & 24.by benzylic oxidation followed by known bromination and elimination processes.

Scheme 3

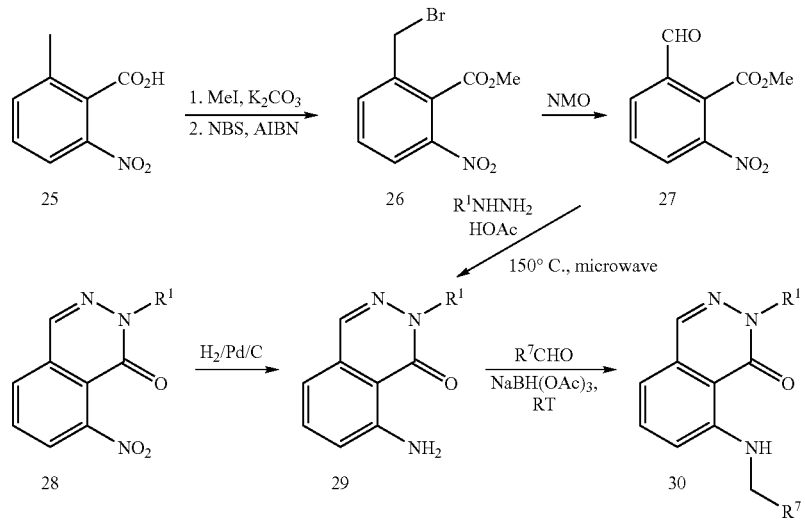

Compounds of Formula I can be prepared by the procedure described in Scheme 3 wherein a 2-methyl-6-nitro-benzoic acid 25, for example, is esterified followed by benzylic bromination and oxidation to the aldehyde 27. Reaction of the aldehyde 27 with a hydrazine followed by cyclization affords the nitro-phthalazinone 28. The nitro-phthalazinone 28 can be reduced under standard hydrogenation conditions and reacted with an aldehyde to afford compounds of Formula I 30.

Scheme 4

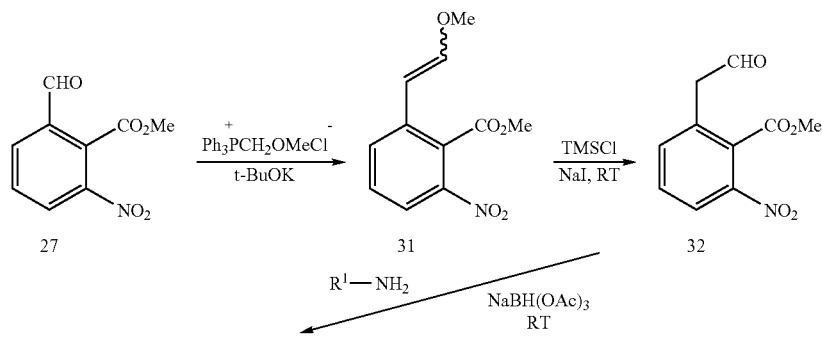

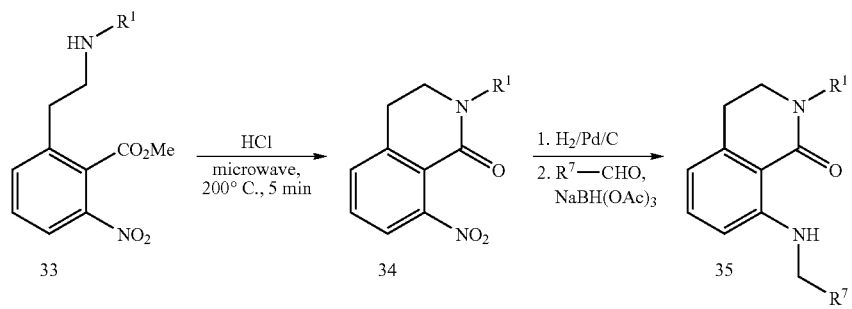

Compounds of Formula II can be prepared by the procedure shown in Scheme 4 wherein the same aldehyde 27 described in Scheme 1, for example, is reacted under standard Wittig conditions to give the enol-ether 31 which is then converted by known processes to the homologated aldehyde 32. Reaction of the aldehyde 32 with an amine such as an aniline affords a phenethyl amine 33 which is then cyclized under acidic conditions to give the nitro-quinolinone 34. The nitro-quinolinone 34 can be reduced under standard hydrogenation conditions and then reacted with an aldehyde to prepare compounds of Formula II 35.

Scheme 5

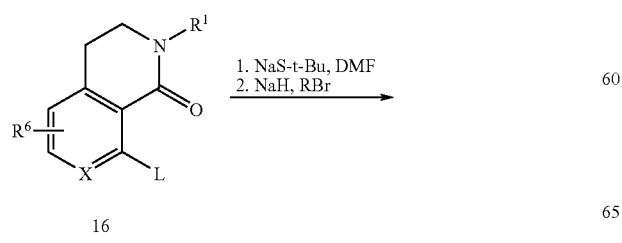

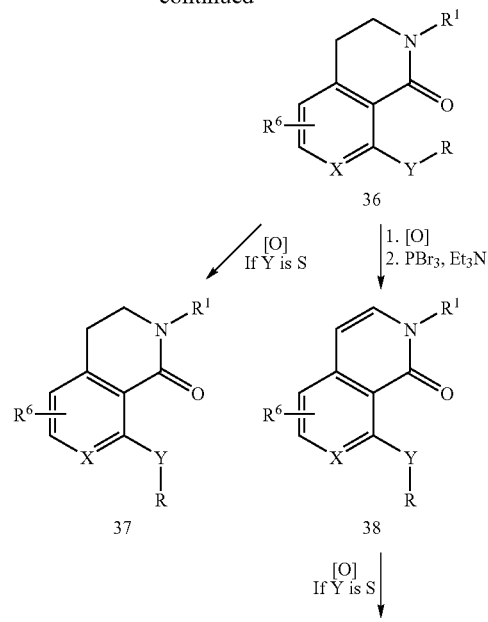

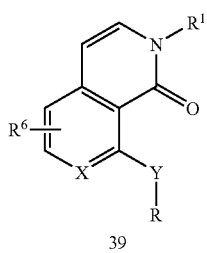

39

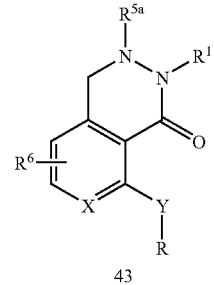

43

Compounds of Formula I can be prepared by the procedure described in Scheme 5 wherein X is CH, Y is O, S, SO or $SO_2$, and L is OMe or SMe, similar to that described by A. Pinchart, et al., Tetrahedron Letters, 40:5479-5482 (1999). The alkoxy or thioxy derivatives 16 (L=OMe or SMe) are reacted, after deprotection, with a suitable bromide and standard alkylation conditions, such as with base and substituted halides to form the 3,4-dihydro-2H-isoquinolin-1-one 36. If Y=S, the thiol can be oxidized to the sulfone or sulfoxide 37. In addition, the 3,4-dihydro-2H-isoquinolin-1-one 36 can be converted to the corresponding 2H-isoquinolin-1-one 38 by benzylic oxidation followed by known bromination and elimination processes. If Y=S, the thiol 38 can be oxidized to the sulfone or sulfoxide 39.

Compounds of Formula I can be prepared by the procedure described in Scheme 6 wherein Y is O, S, SO or $SO_2$, and L is OMe or SMe, similar to that described by A. Pinchart, et al., Tetrahedron Letters, 40:5479-5482 (1999). The alkoxy or thioxy derivatives 4 (L=OMe or SMe) are reacted, after deprotection, with a suitable bromide and standard alkylation conditions, such as with base and substituted halides to form the 3,4-dihydro-2H-azaisoquinolin-1-one 40. If Y=S, the thiol can be oxidized to the sulfone or sulfoxide 41. In addition, the 3,4-dihydro-2H-azaisoquinolin-1-one 40 can be converted to the corresponding 2H-azaisoquinolin-1-one 42 such as by reductive amination. If Y=S, the thiol 42 can be oxidized to the sulfone or sulfoxide 43.

The starting compounds defined in Schemes 1-6 may also be present with functional groups in protected form if necessary and/or in the form of salts, provided a salt-forming group is present and the reaction in salt form is possible. If so desired, one compound of Formula I can be converted into another compound of Formula I or a N-oxide thereof; a compound of Formula I can be converted into a salt; a salt of a compound of Formula I can be converted into the free compound or another salt; and/or a mixture of isomeric compounds of Formula I can be separated into the individual isomers.

N-Oxides can be obtained in a known matter by reacting a compound of Formula I with hydrogen peroxide, oxone, or a peracid, e.g. 3-chloroperoxy-benzoic acid, in an inert solvent, e.g. dichloromethane, or a mixture of water and an alcohol such as MeOH or EtOH, at a temperature between about −10-35° C., such as about 0° C.-RT.

If one or more other functional groups, for example carboxy, hydroxy, amino, or mercapto, are or need to be protected in a compound of Formula I or in the preparation of compounds of Formula I, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard ref-

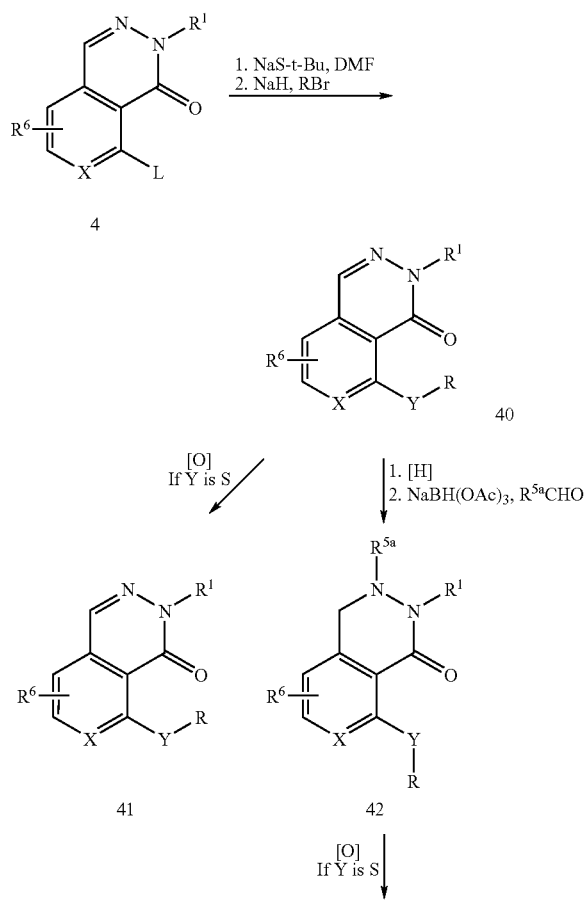

Scheme 6 erence works, such as J. F. W. McOmie, Protective Groups in Organic Chemistry, Plenum Press, London and New York (1973), in T. W. Greene, Protective Groups in Organic Synthesis, Wiley, N.Y. (1981), in The Peptides, Volume 3, eds. E. Gross and J. Meienhofer, Academic Press, London and New York (1981), in Methoden der organischen Chemie (Methods of Organic Chemistry), Houben Weyl, 4th edition, Volume 15/1, Georg Thieme Verlag, Stuttgart (1974), in H-D. Jakubke and H. Jescheit, Aminosauren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

In the additional process steps, carried out as desired, functional groups of the starting compounds which should not take part in the reaction may be present in unprotected form or may be protected, for example, by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example, a monohalogenide); this may be done by heating to a melt, or for example by heating as a solid under a high vacuum at elevated temperature, for example from 130 to 170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H$^+$ form, depending on the type of reaction and/or reactants at reduced, normal, or elevated temperature, for example in the range from about −100° C. to about 190° C., preferably from about −80° C. to about 150° C., for example at about −80° C. to about 60° C., at RT, at about −20° C. to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., EtOAc, ethers, typically aliphatic ethers, e.g., Et$_2$O, or cyclic ethers, e.g., THF, liquid aromatic hydrocarbons, typically benzene or toluene, alcohols, typically MeOH, EtOH or 1-propanol, IPOH, nitrites, typically CH$_3$CN, halogenated hydrocarbons, typically CH$_2$Cl$_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

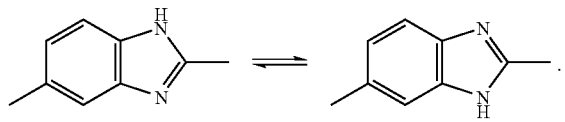

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition. (2001); M. Bodanszky, A. Bodanszky: The Practice of Peptide Synthesis, Springer-Verlag, Berlin Heidelberg (1984); J. Seyden-Penne: Reductions by the Alumino- and Borohydrides in Organic Synthesis, 2$^{nd}$ edition, Wiley-VCH (1997); and L. Paquette, ed., Encyclopedia of Reagents for Organic Synthesis, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formula I. These detailed descriptions fall within the scope, and serve to exemplify, the above-described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company. Unless otherwise noted, all materials were obtained from commercial suppliers and used without further purification. Anhydrous solvents such as DMF, THF, $CH_2Cl_2$ and toluene were obtained from the Aldrich Chemical Company. All reactions involving air- or moisture-sensitive compounds were performed under a nitrogen atmosphere. Flash chromatography was performed using Aldrich Chemical Company silica gel (200-400 mesh, 60A) or Biotage pre-packed column. Thin-layer chromatography (TLC) was performed with Analtech gel TLC plates (250µ). Preparative TLC was performed with Analtech silica gel plates (1000-2000µ). Preparative HPLC was conducted on a Beckman or Waters HPLC system with 0.1% TFA/$H_2O$ and 0.1% TFA/$CH_3CN$ as mobile phase. The flow rate was at 20 mL/min. and gradient method was used. All examples were purified to >90% purity as determined by high-performance liquid chromatography. All compounds showed NMR spectra consistent with their assigned structures. Unless otherwise indicated all $^1H$ NMR spectra were run on a Bruker 400 MHz instrument. Mass spectral data was determined by electrospray ionization technique. Mass spectra (MS) were determined on a Perkin Elmer—SCIEX API 165 electrospray mass spectrometer (positive and/or negative) or an HP 1100 MSD LC-MS with electrospray ionization and quadrupole detection. Microwave synthesis was performed in a Personal Chemistry™ Smith Synthesizer. All parts are by weight, reactions were run at RT and temperatures are in Degrees centigrade unless otherwise indicated.

The following abbreviations are used:
AcOH, HOAc—acetic acid
AIBN—2,2-azobisisobutyronitrile
atm—atmosphere
$CH_3CN$—acetonitrile
ATP—adenosine triphosphate
$NH_4Cl$ ammonium chloride
$NH_4OH$—ammonium hydroxide
BINAP—2,2'-bis(diphenylphosphino)-1,1'binaphthyl
$BH_3$—borane
BSA—bovine serum albumin
$CCl_4$—carbon tetrachloride TMSCl—4-chlorotrimethylsilane
DDQ—2,3-dichloro-5,6-dicyano-1,4-benzoquinone
CH$_2$Cl$_2$—dichloromethane
DEA—diethylamine
DIEA—diisopropylethylamine
DIAD—diisopropyl azodicarboxylate
EDC—1-(3-dimethylaminopropyl)-3-ethylcarbodiimide hydrochloride
DMF—dimethylformamide
DMSO—dimethyl sulfoxide
DPPA—diphenylphosporyl azide
DMAP—dimethylaminopyridine
DEAD—diethylazidocarboxylate
DTT—dithiothreitol
EtOH—ethanol
EtOAc—ethyl acetate
Et$_2$O—ethyl ether
eq—equivalent
FeSO$_4$—ferric sulfate
g—gram
h—hour
HBr—hydrobromic acid
HCl—hydrochloric acid
H$_2$—hydrogen
HOBt—hydroxybenzotriazole
iPrOH—isopropanol
LAH—lithium aluminum hydride
LDA—lithium diisopropylamide
LiOH—lithium hydroxide
m-CPBA—m-chloroperbenzoic acid
MgSO$_4$—magnesium sulfate
MnCl$_2$—manganese chloride
MeOH—methanol
Ph$_3$P$^+$CH$_2$OmeCl$^-$—(methoxymethyl)-triphenylphosphonium chloride
MeI—methyl iodide
NMO—4-methylmorpholine N-oxide
CH$_3$NH$_2$—methylamine
HNO$_3$—nitric acid
mg—milligram
mL—milliliter
min—minutes
NBS—N-bromosuccinimide
N$_2$—nitrogen
Pd/C—palladium on carbon
Pd(OAc)$_2$—palladium acetate
Pd(PPh$_3$)$_4$—palladium tetrakis triphenylphosphine
Pd$_2$(dba)$_3$—tris(dibenzylideneacetone)di-palladium
POCl$_3$—phosphoryl chloride
PCl$_5$—phosphorous pentachloride
P$_2$O$_5$—phosphorous pentoxide
PBr$_3$—phosphorous tribromide
psi—pounds per square inch
Pt/C—platinum on carbon
K$_2$CO$_3$—potassium carbonate
KNO$_3$—potassium nitrate
t-BuOK—potassium t-butoxide
RT—room temperature
NaOAc—sodium acetate
NaHCO$_3$—sodium bicarbonate
NaBH$_4$—sodium borohydride
Na$_2$CO$_3$—sodium carbonate
NaCl—sodium chloride
NaCN—sodium cyanide
NaCNBH$_3$—sodium cyanoborohydride
NaH—sodium hydride
NaOH—sodium hydroxide
NaI—sodium iodide
NaNO$_3$—sodium nitrate
Na$_2$SO$_4$—sodium sulfate
NaOt-Bu—sodium t-butoxide
NaHB(OAc)$_3$—sodium triacetoxyborohydride
H$_2$SO$_4$—sulfuric acid
Bu$_4$NBr tetrabutyl ammonium bromide
Bu$_4$NI—tetrabutyl ammonium iodide
t-BuOH—tert-butyl alcohol
t-BuOMe, MTBE—tert-butylmethylether
Boc—tert-butyloxycarbonyl
THF—tetrahydrofuran
TEA, Et$_3$N—triethylamine
TFA—trifluoroacetic acid
PPh$_3$—triphenylphosphine
H$_2$O—water
PS-TsNHNH$_2$—polystyrene tosyl hydrazine

EXAMPLE 1

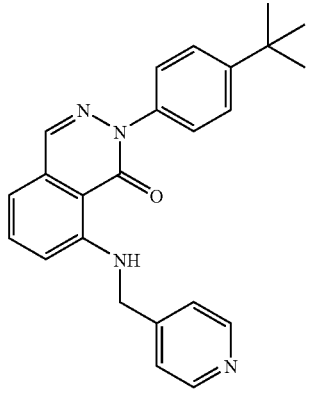

2-(4-(1,1-Dimethylethyl)phenyl)-8-((4-pyridinylmethyl)amino)-1(2H)-phthalazinone Step A: Preparation of methyl 2-methyl-6-nitro-benzoate To a solution of the 2-methyl-6-nitro-benzoic acid (5.6 g, 30.9 mmol, 1.0 eq, Aldrich) and acetone (100 mL) was added crushed K$_2$CO$_3$ (21.4 g, 154.6 mmol, 5 eq) and MeI (9.6 mL, 154.6 mmol, 5.0 eq.). The reaction was heated to reflux for 15 h then cooled to RT, filtered and concentrated in vacuo. The filtrate was dissolved in EtOAc, washed with H$_2$O and brine, dried (MgSO$_4$) and concentrated in vacuo to give the desired compound as a reddish-brown oil which upon standing at RT crystallized as tan needles.

Step B: Preparaton of 2-bromomethyl-6-nitro-benzoic acid methyl ester

To a solution of methyl 2-methyl-6-nitro-benzoate (Step A, 21 g, 108 mmol) and CCl$_4$ (200 mL) was added NBS (3 g, 17 mmol) and AIBN (1 g, 6 mmol). The reaction was heated to reflux. Each h afterward, 3 g of NBS and 1 g of AIBN was added until a total of 22.2 g of NBS and 6.3 g of AIBN was added. The reaction was stirred for a total of 18 h. The mixture was cooled and filtered to remove a white precipitate. The filtrate was concentrated in vacuo and extracted with EtOAc. The organic layer was washed with H$_2$O and brine (3× each), dried (MgSO$_4$) and concentrated in vacuo to give the crude compound as an orange oil. After 2 days at 20° C. the crude material crystallized. These crystals were washed with Et$_2$O and filtered to give the desired bromide. The filtrate was concentrated in vacuo without heat to half-volume whereupon a yellow precipitate formed which was filtered to afford additional bromide Step C: Preparation of 2-formyl-6-nitro-benzoic acid methyl ester To a stirring suspension of flame-dried 4 Å molecular sieves in $CH_3CN$ (50 mL) was added NMO (2.9 g, 25 mmol). After 5 min, the benzyl bromide (Step B, 3.1 g, 11 mmol) in $CH_3CN$ (5 mL) was added. The reaction was stirred at RT for 1.5 h, filtered through silica gel, eluted with EtOAc and concentrated in vacuo to give a reddish brown oil. Purification by silica flash chromatography (0-30% EtOAc:hexane) gave the desired aldehyde as a white solid Step D: Preparation of 2-(4-tert-butyl-phenyl)-8-nitro-2H-phthalazin-1-one A solution of the aldehyde (Step C, 0.58 g, 3.3 mmol), 4-t-butylphenylhydrazine-HCl (0.66 g, 3.3 mmol), AcOH (1 mL), and dioxane (3 mL) in a sealed reaction vial was heated at 200° C. for 20 min in a microwave. Upon cooling, the residue was diluted with EtOAc (10 mL), then hexane (10 mL). The resulting precipitate was filtered to afford the desired compound as a tan solid. MS m/e 324 $(M+H)^+$. Calc'd for $C_{18}H_{17}N_3O_3$-323.35.

Step E: Preparation of 8-amino-2-(4-tert-butyl-phenyl)-2H-phthalazin-1-one

A solution of the nitro compound (Step D) and EtOAc (10 mL) was hydrogenated over 10% Pd/C (20 mg) at RT and at atmospheric pressure. After 4 h, the mixture was filtered through Celite® and concentrated in vacuo to afford the desired compound as an orange oil. MS m/e 294 $(M+H)^+$. Calc'd for $C_{18}H_{19}N_3O$: 293.15.

Step F: Preparation of 2-(4-tert-butyl-phenyl)-8-[(pyridin-4-ylmethyl)-amino]-2H-phthalazin-1-one To a solution of the amine (Step E, 45 mg, 0.15 mmol) and $CH_2Cl_2$ (10 mL) was added 4-pyridinecarboxaldehyde (0.04 mL, 0.39 mmol) and $NaBH(OAc)_3$ (95 mg, 0.45 mmol). The reaction was stirred at RT for 7 h then quenched with $H_2O$ and extracted with $CH_2Cl_2$. The organic layer was washed with $H_2O$ and brine, dried ($MgSO_4$) and concentrated in vacuo to give the crude product as an orange oil. The crude product was dissolved in 10 mL $CH_2Cl_2$ and stirred with PS-TsNHNH$_2$ resin to remove un-reacted aldehyde. After 1 h, the mixture was filtered through Celite® and concentrated in vacuo. The residue was purified by silica flash chromatography (20-75% EtOAc:hexane) to give the desired product as a light-yellow crystalline solid. MS m/e 385 $(M+H)^+$. Calc'd for $C_{24}H_{24}N_4O$-384.47.

EXAMPLE 2

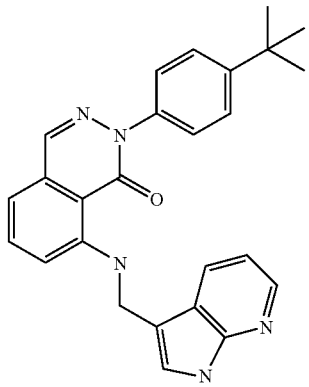

2-(4-(1,1-Dimethylethyl)phenyl)-8-((1H-pyrrolo[2,3-b]pyridin-3-ylmethyl)amino)-1(2H)-phthalazinone To a solution of 8-amino-2-(4-tert-butyl-phenyl)-2H-phthalazin-1-one (Example 1, Step E, 0.36 g, 1.1 mmol, 1 eq) and $CH_2Cl_2$ (50 mL) was added 1H-pyrrolo[2,3-b]pyridine-3-carbaldehyde (0.16 g, 1.1 mmol, 1 eq) and $NaBH(OAc)_3$ (0.72 g, 3.4 mmol, 3.0 eq). The reaction was stirred at RT for 12 h then quenched with $H_2O$ and extracted with $CH_2Cl_2$. The organic layer was washed with $H_2O$ and brine, dried ($MgSO_4$) and concentrated in vacuo. The residue was purified by silica flash chromatography (10-75% EtOAc:hexane) to give the desired product as a yellow solid. MS m/e 424 $(M+H)^+$. Calc'd for $C_{26}H_{25}N_5O$-423.51.

EXAMPLE 3

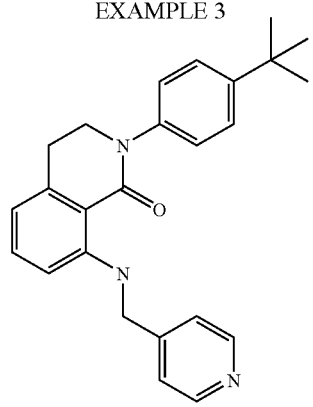

2-(4-(1,1-Dimethylethyl)phenyl)-8-((4-pyridinylmethyl)amino)-3,4-dihydro-1(2H)-isoquinolinone Step A: Preparation of 2-(2-methoxy-vinyl)-6-nitro-benzoic acid methyl ester t-BuOK (5.5 g, 58 mmol, 2 eq) was added portion-wise to a stirred suspension of $Ph_3P^+CH_2OMeCl^-$ (21.7 g, 63 mmol, 2.2 eq) in THF (100 mL) under $N_2$ in an ice-bath. After stirring the red solution at RT for 30 min, 2-formyl-6-nitro-benzoic acid methyl ester (Example 1, Step C, 5.1 g, 29 mmol, 1 eq) in THF (15 mL) was added. The reaction was stirred at RT for 1 h, quenched with saturated $NH_4Cl$ and extracted with EtOAc. The organic layer was washed with $H_2O$ (2×), dried ($MgSO_4$) and concentrated in vacuo to give a dark oil. Purification by silica flash chromatography (0-20% EtOAc:hexane) gave the desired compound as a yellow oil (a mixture of ca. 1.7:1 E/Z isomers).

Step B: Preparation of 2-nitro-6-(2-oxo-ethyl)-benzoic acid methyl ester

To a solution of 2-(2-methoxy-vinyl)-6-nitro-benzoic acid methyl ester (Step A, 3.33 g, 14.1 mmol, 1.0 eq) and $CH_3CN$ (20 mL) was added NaI (2.3 g, 15.5 mmol, 1.1 eq) and TMSCl (2 mL, 15.5 mmol, 1.1 eq). The reaction was stirred at RT for 4 h, then quenched with saturated $NH_4Cl$ and extracted with EtOAc. The organic layer was washed with $H_2O$ and brine, dried ($MgSO_4$) and concentrated in vacuo to give a red-orange oil. Purification by silica flash chromatography (0-30% EtOAc:hexane) gave the desired compound as an orange oil.

Step C: Preparation of 2-[2-(4-tert-butyl-phenylamino)-ethyl]-6-nitro-benzoic acid methyl ester To a solution of the aldehyde (Step B, 0.51 g, 2.3 mmol, 1 eq) and $CH_2Cl_2$ (30 mL) was added 4-t-butyl-aniline (0.36 mL, 2.3 mmol, 1 eq) and $NaBH(OAc)_3$ (1.5 g, 6.8 mmol, 3.0 eq). The mixture was stirred at RT for 18 h then quenched with $H_2O$. The mixture was extracted with EtOAc, the organic layer was washed with brine, dried ($MgSO_4$) and concentrated in vacuo to give an orange oil. Purification by silica flash chromatography gave the desired compound as a yellow-orange foam. MS m/e 357 $(M+H)^+$. Calc'd for $C_{20}H_{24}N_2O_4$-356.42.

Step D: Preparation of 2-(4-tert-butyl-phenyl)-8-nitro-3,4-dihydro-2H-isoquinolin-1-one A solution of the amine (Step C, 0.41 g, 1.2 mmol), conc. HCl (0.1 mL), and dioxane (4 mL) was heated in a microwave at 200° C. for 5 min. The mixture was concentrated in vacuo to give the crude compound as a red oil. Purification by silica flash chromatography (0-25% EtOAc:hexane) gave the desired compound as a yellow oil. MS m/e 325 (M+H)$^+$. Calc'd for $C_{19}H_{20}N_2O_3$-324.37.

Step E: Preparation of 8-amino-2-(4-tert-butyl-phenyl)-3,4-dihydro-2H-isoquinolin-1-one A solution of the nitro compound (Step D, 100 mg, 0.31 mmol) and EtOAc (5 mL) was hydrogenated over 10% Pd/C (20 mg) at atmospheric pressure and RT. After 3 h, the mixture was filtered through Celite® and concentrated in vacuo. Purification by silica flash chromatography (0-15% EtOAc:hexane) gave the desired compound as a white solid. MS m/e 295 (M+H)$^+$. Calc'd for $C_{19}H_{22}N_2O$-294.17.

Step F: Preparation of 2-(4-tert-butyl-phenyl)-8-[(pyridin-4-ylmethyl)-amino]-3,4-dihydro-2H-isoquinolin-1-one To a solution of the amine (Step E) and $CH_2Cl_2$ (5 mL) was added 4-pyridinecarboxaldehyde and $NaBH(OAc)_3$. The reaction was stirred at RT for 18 h. Purification by silica flash chromatography (25-75% EtOAc:hexane) gave the desired product as a light-yellow oil. MS m/e 386 (M+H)$^+$. Calc'd for $C_{25}H_{27}N_3O$-385.50.

Other compounds included in this invention are set forth in Tables 1-4 below.

TABLE 1

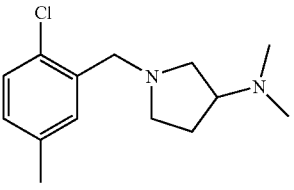

| # | R$^1$ | R | X | Y | Z |
|---|---|---|---|---|---|
| 4. | 4-chlorophenyl | 4-pyridyl-CH$_2$— | N | NH | CH |
| 5. | 5-benzimidazolyl | 3-pyridyl-(CH$_2$)$_2$— | N | O | CH |
| 6. | 2-chlorophenyl | 4-pyridyl-CH$_2$— | N | NMe | CH |
| 7. | 2-quinolinyl | 4-pyridyl-CH$_2$— | N | NMe | CH |
| 8. | 2-benzthiazolyl | 4-pyridyl | N | (CH$_2$)$_2$— | CH |
| 9. | 2-benzimidazolyl | 3-CH$_3$NH(C=O)—4-pyridyl-CH$_2$— | N | NMe | N |
| 10. | 4-fluorophenyl | 6-indazolyl | N | CH=CH— | N |
| 11. | 3-chlorophenyl | 4-quinolyl-CH$_2$— | N | SO$_2$ | N |
| 12. | 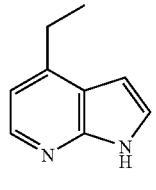 | 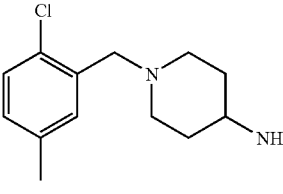 | CH | NH | N |
| 13. | 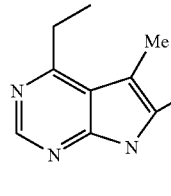 | 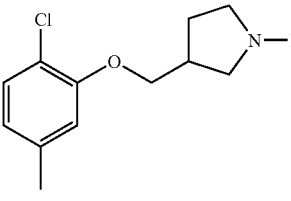 | CH | NH | CH |
| 14. | 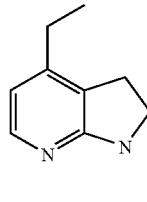 | 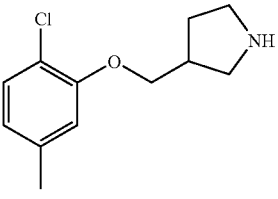 | CH | CH=CH— | N |
| 15. | 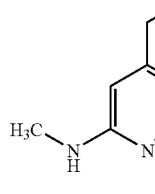 | | CH | CH=CH— | CH |

TABLE 2

| # | R¹ | R⁷ |
|---|---|---|
| 16. | 2-chlorophenyl | 4-pyridyl |
| 17. | 5-benzimidazolyl | 4-pyridyl |
| 18. | 4-chlorophenyl | 4-pyridyl |
| 19. | 2-quinolinyl | 4-pyridyl |
| 20. | 2-benzthiazolyl | 4-pyridyl |
| 21. | 6-benzimidazolyl | 3-CH$_3$NH(C=O)-4-pyridyl |
| 22. | 4-chlorophenyl | 3-CH$_3$NH(C=O)-4-pyridyl |
| 23. | 3,4-dichlorophenyl | 3-CH$_3$NH(C=O)-4-pyridyl |
| 24. | 4-fluorophenyl | 4-quinolyl |
| 25. | 3-chlorophenyl | 4-quinolyl |
| 26. | 2-chloro-5-methylphenyl-O-CH$_2$CH$_2$-pyrrolidinyl | 3-CH$_3$(C=O)NH-phenyl |
| 27. | 3-fluorophenyl | 4-quinolyl |
| 28. | 3-fluoro-4-methoxyphenyl | 4-quinolyl |
| 29. | 3-fluoro-4-methylphenyl | 4-quinolyl |
| 30. | 4-bromophenyl | 6,7-dimethoxy-4-quinolyl |
| 31. | 4-bromo-3-CF$_3$phenyl | 3-methyl-4-pyridyl |
| 32. | 4-bromophenyl | 3-CH$_3$(C=O)NH-4-pyridyl |
| 33. | 4-phenoxyphenyl | 3-CH$_3$NH(C=O)-phenyl |
| 34. | 3-phenoxyphenyl | 3-CH$_3$NH(C=O)-phenyl |
| 35. | 4-biphenyl | 2-MeNH-4-pyrimidinyl |
| 36. | 4-cyclohexylphenyl | 2-MeNH-4-pyrimidinyl |
| 37. | 5-isoindolyl | 2-MeNH-4-pyrimidinyl |
| 38. | 2-chloro-5-methylphenyl-O-CH$_2$CH$_2$-pyrrolidinyl | 4-pyridyl |
| 39. | 2-chloro-5-methylphenyl-O-CH$_2$CH$_2$-N(3-dimethylamino-pyrrolidinyl) | 6,7-dimethoxy-4-methylquinazolinyl |
| 40. | 2-chloro-5-methylbenzyl-N(4-dimethylamino-piperidinyl) | 3-CH$_3$NH(C=O)-4-pyridyl |

TABLE 2-continued

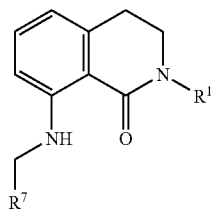

| # | R¹ | R⁷ |
|---|----|----|
| 41. | 2-Cl-5-Me-phenyl-O-CH₂-(1-methylpyrrolidin-2-yl) | 3-CH₃NH(C=O)-4-pyridyl |
| 42. | 2-Cl-5-Me-phenyl-O-CH₂CH₂-pyrrolidin-1-yl | 4-Me-7-azaindol-4-yl |
| 43. | 2-Cl-5-Me-phenyl-CH₂-(4-aminopiperidin-1-yl) | 4-Me-5,6-dimethyl-7-azaindol-4-yl (pyrrolo[2,3-d]pyrimidine) |
| 44. | 2-Cl-5-Me-phenyl-O-CH₂CH₂-(3-dimethylamino-pyrrolidin-1-yl) | 4-Me-7-azaindol-4-yl |
| 45. | 2-Cl-5-Me-phenyl-O-CH₂-(1-isopropylpyrrolidin-3-yl) | 2-MeNH-4-pyrimidinyl |
| 46. | 2-Cl-5-Me-phenyl-O-CH₂-(pyrrolidin-3-yl) | 4-Me-7-azaindol-2(3H)-one |

TABLE 2-continued

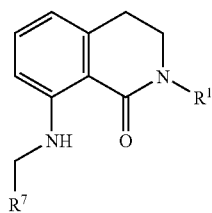

| # | R¹ | R⁷ |
|---|----|----|
| 47. | 2-bromo-5-methylphenyl-O-CH2-(1-methylpyrrolidin-3-yl) | 4-methyl-7-azaindol-5-yl |
| 48. | 2-chloro-5-methylphenyl-O-CH2-(1-methylpyrrolidin-3-yl) | 4-methyl-7-azaindol-5-yl |
| 49. | 2-chloro-5-methylphenyl-O-CH2-(1-methylpyrrolidin-3-yl) | 6-methyl-4-(methylamino)pyrimidinyl |
| 50. | 2-chloro-5-methylphenyl-O-CH2-(piperidin-4-yl) | 4-methyl-7-azaindol-5-yl |
| 51. | 3,4-dichlorophenyl | 4-pyridyl |
| 52. | 3-chloro-4-methylphenyl | 4-pyridyl |
| 53. | 2-chloro-5-methylphenyl-O-CH2-(piperidin-4-yl) | 2,3-dimethyl-4-methyl-7-azaindol-5-yl |
| 54. | 2-chloro-5-methylphenyl-O-CH2CH2-OMe | 4-methyl-7-azaindol-5-yl |

TABLE 2-continued

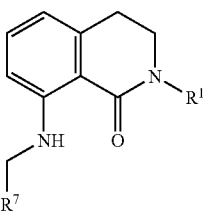

| # | R¹ | R⁷ |
|---|----|----|
| 55. | 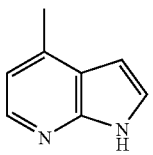 | 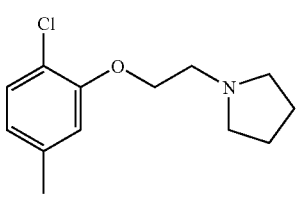 |

TABLE 3

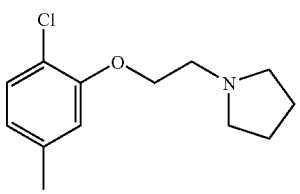

| # | R¹ | R⁷ |
|---|----|----|
| 56. | 2-chlorophenyl | 4-pyridyl |
| 57. | 5-benzimidazolyl | 4-pyridyl |
| 58. | 2-chlorophenyl | 4-pyridyl |
| 59. | 2-quinolinyl | 4-pyridyl |
| 60. | 2-benzthiazolyl | 4-pyridyl |
| 61. | 5-benzimidazolyl | 3-CH₃NH(C=O)-4-pyridyl |
| 62. | 4-chlorophenyl | 3-CH₃NH(C=O)-4-pyridyl |
| 63. | 3,4-dichlorophenyl | 4-pyridyl |
| 64. | 4-fluorophenyl | 4-quinolyl |
| 65. | 3-chlorophenyl | 4-quinolyl |
| 66. | [structure: 2-chloro-5-methylphenyl ether with pyrrolidinylethoxy] | 3-CH₃(C=O)NH-phenyl |
| 67. | 3-fluorophenyl | 4-quinolyl |
| 68. | 3-fluoro-4-methoxyphenyl | 4-quinolyl |
| 69. | 3-fluoro-4-methylphenyl | 4-quinolyl |
| 70. | 4-bromophenyl | 6,7-dimethoxy-4-quinolyl |
| 71. | 4-bromo-3-CF₃phenyl | 3-methyl-4-pyridyl |
| 72. | 4-phenoxyphenyl | 3-CH₃NH(C=O)-phenyl |
| 73. | 4-biphenyl | 2-MeNH-4-pyrimidinyl |
| 74. | 4-cyclohexylphenyl | 2-MeNH-4-pyrimidinyl |
| 75. | 3-isoquinolyl | 2-MeNH-4-pyrimidinyl |
| 76. | 3-quinolyl | 2-MeNH-4-pyrimidinyl |
| 77. | 4-pyrimidinyl | 2-MeNH-4-pyrimidinyl |
| 78. | 5-isoindolyl | 2-MeNH-4-pyrimidinyl |
| 79. | [structure: 2-chloro-5-methylphenyl ether with pyrrolidinylethoxy] | 4-pyridyl |

TABLE 3-continued
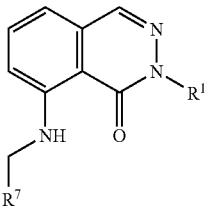
| # | R¹ | R⁷ |
|---|----|----|
| 80. | 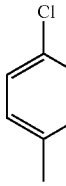 | 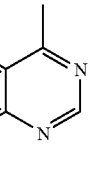 |
| 81. |  | 4-pyridyl |
| 82. | 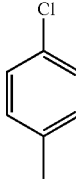 | 4-pyridyl |
| 83. |  | 3-CH₃NH(C=O)-4-pyridyl |
| 84. | 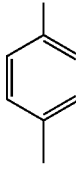 | 2-MeNH-4-pyrimidinyl |
| 85. |  | 2-MeNH-4-pyrimidinyl |

TABLE 3-continued
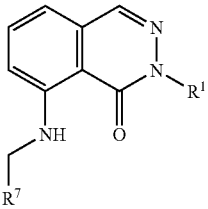
| # | R¹ | R⁷ |
|---|----|----|
| 86. | 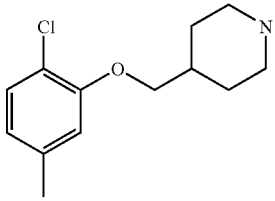 | 4-pyridyl |
| 87. | 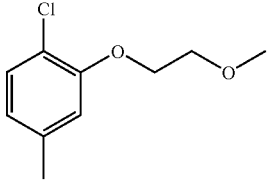 | 3-CH₃NH(C=O)-4-pyridyl |
| 88. | 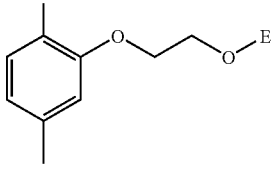 | 2-MeNH-4-pyrimidinyl |
| 89 | 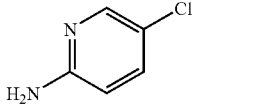 | 2-MeNH-4-pyrimidinyl |
| 90. | 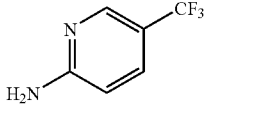 | 4-pyridyl |
| 91. | 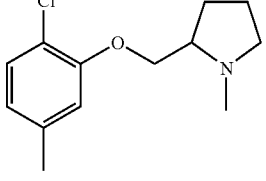 | 3-CH₃NH(C=O)-4-pyridyl |
| 92. | 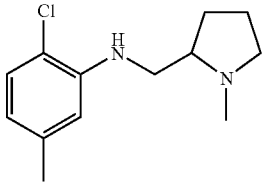 | 4-quinolyl |

TABLE 3-continued
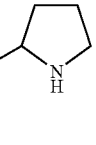
| # | R¹ | R⁷ |
|---|---|---|
| 93. |  | 4-quinolyl |
| 94. | 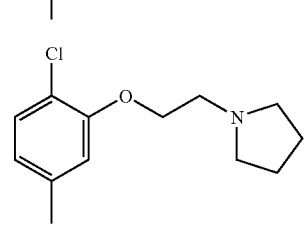 | 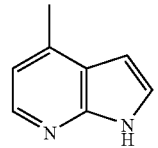 |
| 95. | 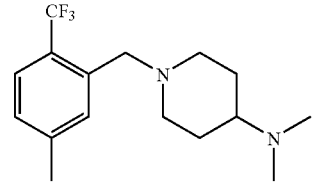 | 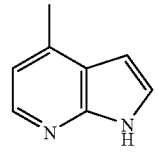 |
| 96. | 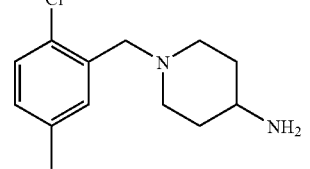 | 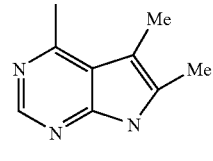 |
| 97. | 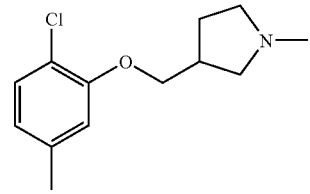 | 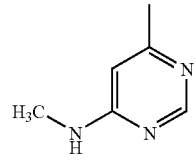 |
| 98. | 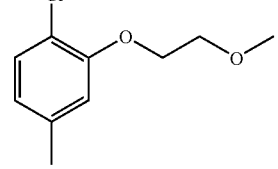 | 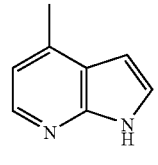 |
| 99. | 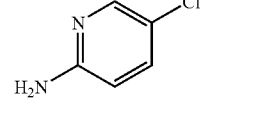 | 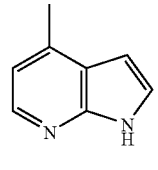 |

TABLE 3-continued
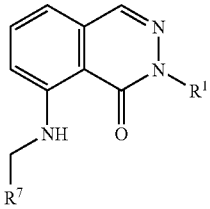
| # | R¹ | R⁷ |
|---|---|---|
| 100. | 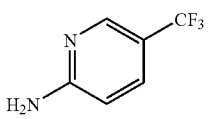 | 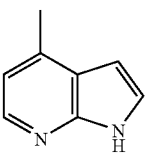 |
TABLE 4
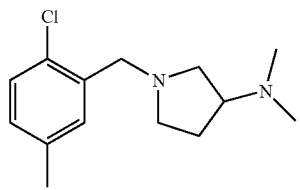
| # | R¹ | R | X | Y | Z |
|---|---|---|---|---|---|
| 101. | 4-chlorophenyl | 4-pyridyl-CH₂— | N | NH | CH₂ |
| 102. | 5-benzimidazolyl | 3-pyridyl-(CH₂)₂— | N | O | CH₂ |
| 103. | 2-chlorophenyl | 4-pyridyl-CH₂— | N | NNe | CH₂ |
| 104. | 2-quinolinyl | 4-pyridyl-CH₂— | N | NMe | CH₂ |
| 105. | 2-benzthiazolyl | 4-pyridyl | N | (CH₂)₂— | CH₂ |
| 106. | 2-benzimidazolyl | 3-CH₃NH(C=O)—4-pyridyl-CH₂— | N | NMe | NH |
| 107. | 4-fluorophenyl | 6-indazolyl | N | CH=CH— | NH |
| 108. | 3-chlorophenyl | 4-quinolyl-CH₂— | N | SO₂ | NH |
| 109. | 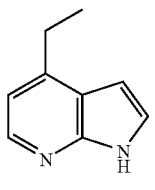 | 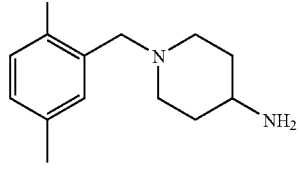 | CH | NH | NH |
| 110. | 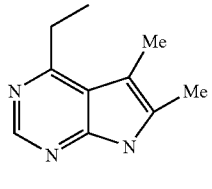 | 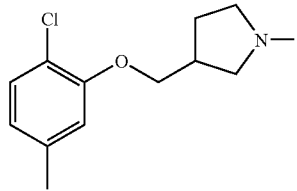 | CH | NH | CH₂ |
| 111. | 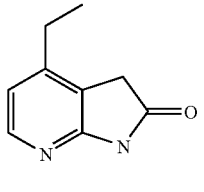 |  | CH | CH=CH— | NH |

TABLE 4-continued

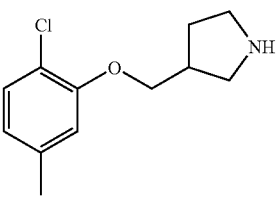

| # | R¹ | R | X | Y | Z |
|---|----|---|---|---|---|
|   | 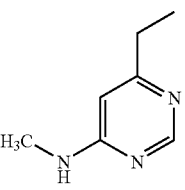 |   | CH | CH=CH— | CH$_2$ |

Although the pharmacological properties of the compounds of Formulas I-III vary with structural change, in general, activity possessed by compounds of Formula I-III may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of KDR kinase at doses less than 50 μM.

BIOLOGICAL EVALUATION

KUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+ antibiotics, and spun at 1000 rpm for 10 min. Prior to centrifugation of the cells, a small amount is collected for a cell count. After centrifugation, the medium is discarded, and the cells are resuspended in the appropriate volume of DMEM+ 10% FBS+antibiotics to achieve a concentration of 3×10$^5$ cells/mL. Another cell count is performed to confirm the cell concentration. The cells are diluted to 3×10$^4$ cells/mL in DMEM+10% FBS+antibiotics, and 100 μL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 μL of each compound dilution are diluted further in a total of 1 mL DMEM+ 10% FBS+antibiotics (400× dilution). Medium containing 0.25% DMSO is also prepared for the 0 μM compound sample. At the 22 h timepoint, the medium is removed from the cells, and 100 μL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 μL of each will be added to the cells (110 μL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. IC$_{50}$ values are then determined.

Examples 1-3 inhibited VEGF-stimulated HUVEC proliferation at a level below 500 nm.

Angiogenesis Model

To determine the effects of the present compounds on angiogenesis in vivo, selective compounds are tested in the rat corneal neovascularization micropocket model or the angiogenesis assay of Passaniti, Lab. Invest., 67:519-528 (1992).

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+5% Isofluorane). An othoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After 24 h in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A. G. Heinz, Irvine Calif.) mounted on a Nikon SMZ-U stereo microscope (A. G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:

0.1% BSA in PBS vehicle: 0.025 g of BSA was added to 25.0 mL of sterile 1× phosphate buffered saline, gently shaken until fully dissolved, and filtered at 0.2 µm. Individual 1.0 mL samples were aliquoted into 25 single use vials, and stored at −20° C. until use. For the rHu-bFGF disks, a vial of this 0.1% BSA solution was allowed to thaw at RT. Once thawed, 10 µL of a 100 mM stock solution of DTT was added to the 1 mL BSA vial to yield a final concentration of 1 mM DTT in 0.1% BSA.

rHu-VEGF Dilutions:

Prior to the disk implant surgery, 23.8 µL of the 0.1% BSA vehicle above was added to a 10 µg rHu-VEGF lyophilized vial yielding a final concentration of 10 µM.

rHu-bFGF: Stock concentration of 180 ng/µL:

R&D rHu-bFGF: Added 139 µL of the appropriate vehicle above to the 25 µg vial lyophilized vial. 13.3 µL of the [180 ng/µL] stock vial and added 26.6 µL of vehicle to yield a final concentration of 3.75 µM concentration.

Nitro-cellulose disk preparation: The tip of a 20-gauge needle was cut off square and beveled with emery paper to create a punch. This tip was then used to cut out ≈0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention are active at doses less than 150 mpk.

Rat Adjuvant Arthritis Model

The rat adjuvant arthritis model (Pearson, Proc. Soc. Exp. Biol. 91:95-101 (1956)) is used to test the anti-arthritic activity of compounds of the Formula I, or salts thereof. Adjuvant Arthritis can be treated using two different dosing schedules: either (i) starting time of immunization with adjuvant (prophylactic dosing); or from day 15 when the arthritic response is already established (therapeutic dosing). Preferably a therapeutic dosing schedule is used.

Rat Carrageenan-Induced Analgesia Test

The rat carrageenan analgesia test was performed with materials, reagents and procedures essentially as described by Hargreaves, et al., Pain, 32:77 (1988). Male Sprague-Dawley rats were treated as previously described for the Carrageenan Foot Pad Edema test. 3 h after the injection of the carrageenan, the rats were placed in a special plexiglass container with a transparent floor having a high intensity lamp as a radiant heat source, positionable under the floor. After an initial 20 min period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined.

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable topological effects are expected when compounds of the present invention are administered in accordance with the present invention.

All mentioned references, patents, applications and publications, are hereby incorporated by reference in their entirety, as if here written.

What is claimed is:

1. A compound of Formula I

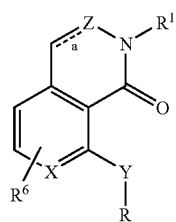

wherein bond a is either a single bond or a double bond;
wherein X is CH;
wherein Y is $NR^4$;
wherein Z is $CR^5$ if bond a is a double bond;
wherein Z is $CHR^5$ if bond a is a single bond;
wherein R is selected from
a) substituted or unsubstituted 6-10 membered aryl,
b) substituted or unsubstituted 4-6 membered heterocyclyl,
c) substituted or unsubstituted 9-14 membered fused heterocyclyl,
d) substituted or unsubstituted aryl-$C_{1-2}$-alkyl,
e) substituted or unsubstituted heterocyclyl-$C_{1-2}$-alkyl, and
f) lower alkyl;
where substituted R is substituted with one or more substituents selected from halo, —$OR^3$, —$SR^3$, —$SO_2R^3$, —$CO_2R^3$, —$C(O)NR^3R^3$, —$C(O)R^3$, —$NR^3R^3$, —$SO_2NR^3R^3$, —$NR^3C(O)OR^3$, —$NR^3C(O)R^3$, optionally substituted 3-6 membered heterocyclyl, optionally substituted phenyl, alkylaminoalkoxyalkoxy, nitro, cyano, oxo, lower alkyl substituted with one or more $R^2$;
wherein $R^1$ is selected from unsubstituted or substituted
a) 6-10 membered aryl,
b) 5-6 membered heterocyclyl,
c) 9-14 membered fused heterocyclyl,
d) cycloalkyl,
e) cycloalkenyl,
f) lower alkyl, and
g) lower alkenyl,
wherein substituted $R^1$ is substituted with one or more substituents independently selected from halo, —$OR^3$, —$SR^3$, —$CO_2R^3$, —$C(O)NR^3R^3$, —$C(O)R^3$, —$NR^3R^3$, oxo, —$OC(O)R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, aminoalkylcarbonylamino, alkylaminoalkylcarbonylamino, alkylaminoalkoxy, alkylaminoalkoxyalkoxy, nitro, and lower alkyl substituted with one or more $R^2$;
wherein $R^2$ is selected from H, halo, —$OR^3$, amino, $C_{1-3}$-alkylamino, $C_{1-3}$-dialkylamino, $C_{1-3}$-alkyl, optionally substituted phenyl, optionally substituted phenyl-$C_{1-3}$-alkyl, 4-6 membered heterocyclyl, and optionally substituted 4-6 membered heterocyclyl-$C_1$-$C_3$-alkyl;
wherein $R^3$ is independently selected from H, lower alkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl and lower haloalkyl;
wherein $R^4$ is independently selected from H, and lower alkyl;
wherein $R^5$ is independently selected from H, —$OR^3$, and lower alkyl;
wherein $R^{5a}$ is independently selected from H, and lower alkyl; and
wherein $R^6$ is selected from H, halo, —$OR^3$, —$SR^3$, —$CO_2R^3$, —$SOR^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, nitro, lower alkyl substituted with one or more $R^2$, lower alkenyl substituted with one or more $R^2$ and lower alkynyl substituted with one or more $R^2$;
or a pharmaceutically acceptable derivative thereof.

2. A compound of claim 1 wherein Y is NH; wherein Z is $CHR^5$ and bond a is a single bond; and wherein $R^5$ is independently selected from H, —OH, and methyl; or a pharmaceutically acceptable derivative thereof.

3. A compound of claim 1 wherein R is unsubstituted or substituted 9-10 membered fused nitrogen-containing heteroaryl and optionally further substituted 9-10 membered fused N-containing oxo-substituted heterocyclyl; or a pharmaceutically acceptable derivative thereof.

4. A compound of claim 3 wherein R is selected from quinolin-4-yl, quinolin-5-yl, quinolin-6-yl, isoquinolin-5-yl, 2-oxo-1,2-dihydroquinol-7-yl, 1-oxo-2,3-dihydro-1H-isoindol-4-yl, quinazolin-6-yl, 4-oxo-3,4-dihydro-quinazolin-6-yl, indazol-5-yl, indazol-6-yl, indol-5-yl, isoindol-4-yl, benzimidazol-5-yl, 2-oxo-2,3-dihydro-1H-benzimidazol-5-yl and benzotriazol-6-yl; wherein R is optionally substituted with one or more substituents selected from chloro, fluoro, amino, hydroxy, methyl, ethyl, propyl, trifluoromethyl, 1-methylpiperidinylmethoxy, dimethylaminoethoxyethoxy, methoxy and ethoxy; or a pharmaceutically acceptable derivative thereof.

5. A compound of claim 1 wherein R is substituted or unsubstituted 6-membered nitrogen containing heteroaryl-$C_{1-2}$-alkyl or 9-10 membered nitrogen containing fused heteroaryl-$C_{1-2}$-alkyl; wherein substituted R is substituted with one or more substituents independently selected from halo, amino, $C_{1-3}$-alkoxy, hydroxyl, $C_{1-3}$-alkyl and $C_{1-2}$-haloalkyl; or a pharmaceutically acceptable derivative thereof.

6. A compound of claim 5 wherein R is substituted or unsubstituted selected from (3-pyridyl)-(CH$_2$)$_2$—, (4-pyridyl)—CH$_2$—, (4-pyrimidinyl)-CH$_2$—, (5-pyrimidinyl)-CH$_2$—, (6-pyrimidinyl)-CH$_2$—, (4-pyridazinyl)-CH$_2$—, (6-pyridazinyl)-CH$_2$—, 5-indazolyl-CH$_2$—, 4-quinolinyl-CH$_2$—, 6-quinolinyl-CH$_2$—, pyrrolo[2,3-b]pyridin-4-yl-CH$_2$—, pyrrolo[2,3-b]pyridin-5-yl-CH$_2$—, 5-isoquinolinyl-CH$_2$— and 4-quinazolinyl-CH$_2$—; wherein R is unsubstituted or substituted with one or more substituents selected from chloro, fluoro, amino, hydroxy, methyl, ethyl, propyl, trifluoromethyl, methoxy and ethoxy; or a pharmaceutically acceptable derivative thereof.

7. A compound of claim 1 wherein R is selected from indazol-6-yl, (3-pyridyl)-(CH$_2$)$_2$—, (4-pyridyl)-CH$_2$—, pyrrolo[2,3-b]pyridin-4-yl-CH$_2$—, pyrrolo[2,3-b]pyridin-5-yl-CH$_2$—, 6-quinolinyl-CH$_2$— and 4-quinolinyl-CH$_2$—; or a pharmaceutically acceptable derivative thereof.

8. A compound of claim 1 wherein $R^6$ is one or more substituents independently selected from H, halo, hydroxy, $C_{1-2}$-alkoxy, $C_{1-2}$-haloalkoxy, amino, $C_{1-2}$-alkylamino, optionally substituted 5-6 membered heterocyclyl-$C_{1-2}$-alkylamino, aminosulfonyl, $C_{3-6}$-cycloalkyl, optionally substituted 5-6 membered heterocyclyl, optionally substituted phenyl, $C_{1-4}$-alkyl, cyano, $C_{1-2}$-hydroxyalkyl, $C_{1-3}$-carboxyalkyl, nitro, $C_{2-3}$-alkenyl, $C_{2-3}$-alkynyl and $C_{1-2}$-haloalkyl; or a pharmaceutically acceptable derivative thereof.

9. A compound of claim 7 wherein $R^6$ is one or more substituents independently selected from H, chloro, fluoro, bromo, hydroxy, methoxy, ethoxy, trifluoromethoxy, amino, dimethylamino, aminosulfonyl, carboxymethyl, cyclopropyl, optionally substituted phenyl, methyl, ethyl, propyl, cyano, hydroxymethyl, nitro, propenyl, propynyl, trifluoromethyl and unsubstituted or substituted heteroaryl selected from thienyl, furanyl, pyridyl, imidazolyl, and pyrazolyl; or a pharmaceutically acceptable derivative thereof.

10. A compound of claim 8 wherein $R^6$ is H; or a pharmaceutically acceptable derivative thereof.

11. A compound of claim 1 wherein $R^1$ is selected from unsubstituted or substituted 9-11 and 14 membered bicyclic saturated or partially saturated heterocyclyl; or a pharmaceutically acceptable derivative thereof.

12. A compound of claim 11 wherein $R^1$ is selected from wherein $R^1$ is selected from 1,2-dihydroquinolyl, 1,2,3,4-tetrahydroquinolinyl, 1,4-benzodioxanyl, 2-oxo-1,2-dihydroquinol-7-yl, 1-oxo-1,2,3,4-tetrahydro-isoquinolyl, 2,3-dihydro-1,1-dioxo-benzo[d]isothiazolyl, 2,3-dihydro-1H-indolyl, 2,3-dihydro-benzofuryl, 1,2,3,4-tetrahydro-isoquinolyl, 2,3,4,4a,9,9a-hexahydro-1H-3-aza-fluorenyl, and 5,6,7-trihydro-1,2,4-triazolo[3,4-a]isoquinolyl; where $R^1$ is unsubstituted or substituted with one or more substituents selected from bromo, chloro, fluoro, iodo, nitro, amino, cyano, aminoethyl, Boc-aminoethyl, hydroxy, oxo, aminosulfonyl, 4-methylpiperazinylsulfonyl, cyclohexyl, phenyl, phenylmethyl, morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2- (1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, fluorosulfonyl, methylsulfonyl, methylcarbonyl, Boc, piperidin-1-ylmethylcarbonyl, 4-methylpiperazin-1-ylcarbonylethyl, methoxycarbonyl, aminomethylcarbonyl, dimethylaminomethylcarbonyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperidin-4-ylmethoxy, piperidin-4-ylmethoxy, 1-methylpiperidin-4-yloxy, isopropoxy, methoxy and ethoxy; or a pharmaceutically acceptable derivative thereof.

13. A compound of claim 1 wherein $R^1$ is selected from unsubstituted or substituted 5-6 and 9-10 membered bicyclic heteroaryl; and pharmaceutically acceptable derivative thereof; in conjunction with any of the above or below embodiments optionally substituted with one or more substituents selected from halo, $C_{1-6}$-alkyl, optionally substituted $C_{3-6}$-cycloalkyl, optionally substituted phenyl, optionally substituted phenyl-$C_1$-$C_4$-alkylenyl, $C_{1-2}$-haloalkoxy, optionally substituted phenyloxy, optionally substituted 4-6 membered heterocyclyl-$C_1$-$C_4$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, $C_{1-4}$-alkylcarbonyl, $C_{1-3}$-alkylamino-$C_{1-3}$-alkylcarbonylamino, $C_{1-3}$-alkylamino-$C_{1-3}$- alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-hydroxyalkyl,

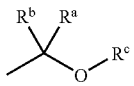

and $C_{1-4}$-alkoxy; wherein $R^c$ is selected from H, methyl, H, piperidinylethyl and methoxyethoxyethyl; and wherein $R^a$ and $R^b$ are independently selected from H and trifluoromethyl; or a pharmaceutically acceptable derivative thereof.

14. A compound of claim 13 wherein $R^1$ is selected from thienyl, indolyl, pyridyl, 2,1,3-benzothiadiazolyl, indazolyl, quinolyl, isoquinolyl, pyrimidinyl, pyridazinyl, pyrazolyl, imidazolyl, oxazolyl, thiazolyl, thiadiazolyl, quinazolinyl, furyl and pyrrolyl; optionally substituted with one or more substituents selected from morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperidin-4-ylmethoxy, piperidin-4-ylmethoxy, 1-methylpiperidin-4-yloxy, 1,1-di(trifluoromethyl)-1-(piperidinylethoxy)methyl, 4-methylpiperazinylsulfonyl, Boc-piperidin-1-ylmethylcarbonyl, 4-methylpiperazin-1-ylcarbonylethyl, dimethylaminomethyl-carbonylamino, bromo, chloro, fluoro, iodo, nitro, amino, cyano, aminoethyl, Boc-aminoethyl, hydroxy, oxo, aminosulfonyl, cyclohexyl, phenyl, phenylmethyl, fluorosulfonyl, methylsulfonyl, methylcarbonyl, methoxycarbonyl, aminomethylcarbonyl, dimethylaminomethylcarbonyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(methoxyethoxyethoxy), 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, isopropoxy, methoxy and ethoxy; or a pharmaceutically acceptable derivative thereof.

15. A compound of claim 1 wherein $R^1$ is selected from phenyl optionally substituted with one or more substituents selected from halo, $C_{1-6}$-alkyl, optionally substituted $C_{3-6}$-cycloalkyl, optionally substituted phenyl, optionally substituted phenyl-$C_{1-C4}$-alkylenyl, $C_{1-2}$-haloalkoxy, optionally substituted phenyloxy, optionally substituted 4-6 membered heterocyclyl-$C_3$-$C_4$-alkyl, optionally substituted 4-6 membered heterocyclyl-$C_2$-$C_4$-alkenyl, optionally substituted 4-6 membered heterocyclyl, optionally substituted 4-6 membered heterocyclyloxy, optionally substituted 4-6 membered heterocyclyl-$C_{1-4}$-alkoxy, optionally substituted 4-6 membered heterocyclylsulfonyl, optionally substituted 4-6 membered heterocyclylamino, optionally substituted 4-6 membered heterocyclylcarbonyl, optionally substituted 4-6 membered heterocyclyl-$C_{1-4}$-alkylcarbonyl, $C_{1-2}$-haloalkyl, $C_{1-4}$-aminoalkyl, nitro, amino, hydroxy, cyano, aminosulfonyl, $C_{1-2}$-alkylsulfonyl, $C_{1-4}$-alkylcarbonyl, $C_{1-3}$-alkylamino-$C_{1-3}$-alkylcarbonylamino, $C_{1-3}$-alkylamino-$C_{1-3}$-alkyl, $C_{1-3}$-alkylamino-$C_{1-3}$-alkoxy, $C_{1-3}$-alkylamino-$C_{1-3}$-alkoxy-$C_{1-3}$-alkoxy, $C_{1-4}$-alkoxycarbonyl, $C_{1-4}$-hydroxyalkyl,

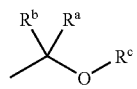

and $C_{1-4}$-alkoxy; wherein $R^c$ is selected from H, methyl, H, piperidinylethyl and methoxyethoxyethyl; and wherein $R^a$ and $R^b$ are independently selected from H and trifluoromethyl; or a pharmaceutically acceptable derivative thereof.

16. A compound of claim 15 wherein $R^1$ is selected from phenyl optionally substituted with one or more substituents selected from morpholinylmethyl, 1-methylpiperazin-4-ylmethyl, 1-methylpiperazin-4-ylpropyl, morpholinylpropyl, piperidin-1-ylmethyl, 1-methylpiperidin-4-ylmethyl, 2-methyl-2-(1-methylpiperidin-4-yl)ethyl, morpholinylethyl, 1-(4-morpholinyl)-2,2-dimethylpropyl, piperidin-4-ylethyl, 1-Boc-piperidin-4-ylethyl, piperidin-1-ylethyl, 1-Boc-piperidin-4-ylethyl, piperidin-4-ylmethyl, 1-Boc-piperidin-4-ylmethyl, piperidin-4-ylpropyl, 1-Boc-piperidin-4-ylpropyl, piperidin-1-ylpropyl, pyrrolidin-1-ylpropyl, pyrrolidin-2-ylpropyl, 1-Boc-pyrrolidin-2-ylpropyl, pyrrolidin-1-ylmethyl, pyrrolidin-2-ylmethyl, 1-Boc-pyrrolidin-2-ylmethyl, pyrrolidinylpropenyl, pyrrolidinylbutenyl, 3-ethoxycarbonyl-2-methyl-fur-5-yl, 4-methylpiperazin-1-yl, 4-methyl-1-piperidyl, 1-Boc-4-piperidyl, piperidin-4-yl, 1-methylpiperidin-4-yl, 1-methyl-(1,2,3,6-tetrahydropyridyl), imidazolyl, morpholinyl, 4-trifluoromethyl-1-piperidinyl, azetidin-3-ylmethoxy, 1-Boc-azetidin-3-ylmethoxy, pyrrol-2-ylmethoxy, 1-Boc-pyrrol-2-ylmethoxy, pyrrol-1-ylmethoxy, 1-methyl-pyrrol-2-ylmethoxy, 1-isopropyl-pyrrol-2-ylmethoxy, 1-Boc-piperidin-4-ylmethoxy, piperidin-4-ylmethoxy, 1-methylpiperidin-4-yloxy, 1,1-di(trifluoromethyl)-1-(piperidinylethoxy)methyl, 4-methylpiperazinylsulfonyl, Boc-piperidin-1-ylmethylcarbonyl, 4-methylpiperazin-1-ylcarbonylethyl, dimethylaminomethyl-carbonylamino, bromo, chloro, fluoro, iodo, nitro, amino, cyano, aminoethyl, Boc-aminoethyl, hydroxy, oxo, aminosulfonyl, cyclohexyl, phenyl, phenylmethyl, fluorosulfonyl, methylsulfonyl, methylcarbonyl, methoxycarbonyl, aminomethylcarbonyl, dimethylaminomethylcarbonyl, hydroxybutyl, methyl, ethyl, propyl, isopropyl, butyl, tert-butyl, sec-butyl, trifluoromethyl, pentafluoroethyl, nonafluorobutyl, dimethylaminopropyl, 1,1-di(trifluoromethyl)-1-hydroxymethyl, 1,1-di(trifluoromethyl)-1-(methoxyethoxyethoxy), 1-hydroxyethyl, 2-hydroxyethyl, trifluoromethoxy, 1-aminoethyl, 2-aminoethyl, 1-(N-isopropylamino)ethyl, 2-(N-isopropylamino)ethyl, dimethylaminoethoxy, 4-chlorophenoxy, phenyloxy, isopropoxy, methoxy and ethoxy; or a pharmaceutically acceptable derivative thereof.

17. A compound of claim 1 wherein $R^1$ is

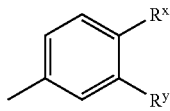

wherein each of $R^x$ and $R^y$ is independently selected from H, bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy, ethoxy, 4-methylpiperazinylsulfonyl, morpholinylmethyl, 4-methylpiperazinylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 3-dimethylaminopyrrolidin- 1-ylmethyl, 1-methylpyrrolidin-2-ylmethyl, dimethylaminoethyl, dimethylaminoethoxy, piperidinylethoxy, morpholinylethyloxy, 4-methylpiperazinylethoxy, 4-isopropylpiperazinylmethoxy, piperidin-4-methoxy, 4-methylpiperidin-1-ylmethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-(N,N-dimethylamino)acetylamino and 2-(N,N-dimethylamino)ethylamino; or a pharmaceutically acceptable derivative thereof.

18. A compound of claim 17 wherein $R^x$ is selected from chloro, tert-butyl, trifluoromethyl, pentafluoroethyl, 1,1di(trifluoromethyl)-1-hydroxymethyl, and trifluoromethoxy; or a pharmaceutically acceptable derivative thereof.

19. A compound of claim 17 wherein each of $R^y$ is selected from H, bromo, chloro, methyl, ethyl, trifluoromethyl, pentafluoroethyl, 1,1-di(trifluoromethyl)-1-hydroxymethyl, trifluoromethoxy, difluoromethoxy, isopropoxy, methoxy, ethoxy, 4-methylpiperazinylsulfonyl, morpholinylmethyl, 4-methylpiperazinylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 3-dimethylaminopyrrolidin-1-ylmethyl, 1-methylpyrrolidin-2-ylmethyl, dimethylaminoethyl, dimethylaminoethoxy, piperidinylethoxy, morpholinylethyloxy, 4-methylpiperazinylethoxy, 4-isopropylpiperazinylmethoxy, piperidin-4-methoxy, 4-methylpiperidin-1-ylmethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-(N,N-dimethylamino)acetylamino and 2-(N,N-dimethylamino)ethylamino; or a pharmaceutically acceptable derivative thereof.

20. A compound of claim 1 wherein $R^1$ is selected from substituted or unsubstituted phenyl-$C_{1-2}$-alkyl; or a pharmaceutically acceptable derivative thereof.

21. A compound of claim 20 wherein $R^1$ is selected from 3-trifluoromethylphenylmethyl, 3-trifluoromethylphenylethyl, 3-methoxyphenylmethyl, phenylethyl, 4-methoxyphenylethyl, 3,4-dimethoxyphenylethyl, 4-methylphenylethyl, 2-fluorophenylethyl, 3-fluorophenylethyl, 2-chlorophenylethyl, 4-chlorophenylethyl, 3,4-dichlorophenylethyl, and 3,5-dichlorophenylethyl; or a pharmaceutically acceptable derivative thereof.

22. A compound of claim 1 of Formula II

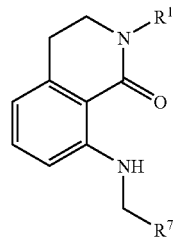

wherein $R^1$ is selected from unsubstituted or substituted
 a) 6-10 membered aryl,
 b) 5-6 membered heterocyclyl,
 c) 9-14 membered fused heterocyclyl, and
 d) phenyl-$C_{1-3}$-alkyl,
 wherein substituted $R^1$ is substituted with one or more substituents independently selected from halo, —$OR^3$, —$SR^3$, —$CO_2R^3$, —$C(O)NR^3R^3$, —$C(O)R^3$, —$NR^3R^3$, oxo, —$OC(O)R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-9 membered heterocyclyl, optionally substituted phenyl, cyano, alkylaminoalkoxy, alkylaminoalkoxyalkoxy, nitro, and lower alkyl substituted with one or more wherein $R^2$ is selected from H, halo, hydroxy, alkoxy, optionally substituted phenyl, optionally substituted phenyl-$C_{1-3}$-alkyl, 4-6 membered heterocyclyl, and optionally substituted 4-6 membered heterocyclyl-$C_{1-C3}$-alkyl;

wherein $R^3$ is independently selected from H, lower alkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl and lower haloalkyl; and wherein $R^7$ is selected from substituted or unsubstituted 6-membered and 9-10 membered heteroaryl; where substituted $R^7$ is substituted with one or more substituents selected from halo, —$OR^3$, —$SR^3$, —$SO_2R^3$, —$CO_2R^3$, —$C(O)NR^3R^3$, —$C(O)R^3$, —$NR^3R^3$, —$SO_2NR^3R^3$, —$NR^3C(O)OR^3$, —$NR^3C(O)R^3$, optionally substituted 3-6 membered heterocyclyl, optionally substituted phenyl, alkylaminoalkoxyalkoxy, nitro, cyano, oxo, lower alkyl substituted with one or more $R^2$;

or a pharmaceutically acceptable derivative thereof.

23. A compound of claim 22 wherein $R^1$ is selected from phenyl substituted with one or more substituents independently selected from halo, —$OR^3$, —$SR^3$, —$CO_2R^3$, —$C(O)NR^3R^3$, —$C(O)R^3$, —$NR^3R^3$, oxo, —$OC(O)R^3$, —$SO_2R^3$, —$SO_2NR^3R^3$, —$NR^3C(O)OR^3$, —$NR^3C(O)R^3$, —$NR^3C(O)NR^3R^3$, optionally substituted $C_{3-6}$-cycloalkyl, optionally substituted 4-6 membered heterocyclyl, optionally substituted phenyl, cyano, $C_{1-3}$-alkylamino-$C_{1-3}$-alkoxy, $C_{1-3}$-alkylamino-$C_{1-3}$-alkoxy-$C_{1-3}$-alkoxy, nitro, and lower alkyl substituted with one or more $R^3$;
 wherein $R^2$ is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4- yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein $R^3$ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-1-yl, piperidin-4-yl and piperazin-4-yl;

or a pharmaceutically acceptable derivative thereof.

24. A compound of claim 23 wherein $R^1$ is selected from phenyl substituted with 1-3 substituents independently selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; or a pharmaceutically acceptable derivative thereof.

25. A compound of claim 22 wherein $R^1$ is selected from substituted or unsubstituted 5-6 membered or 9-10 membered fused partially unsaturated heterocyclyl or heteroaryl; wherein substituted $R^1$ is substituted with one or more substituents independently selected from halo, —$OR^3$, —$SR^3$, —$CO_2R^3$, —$C(O)NR^3R^3$, —$C(O)R^3$, —$NR^3R^3$, oxo, —OC(O)$R^3$, —$SO_2R^3$, —$SO_2NR^3R^3$, —$NR^3C(O)OR^3$, —$NR^3C(O)R^3$, —$NR^3C(O)NR^3R^3$, optionally substituted $C_{3-6}$-cycloalkyl, optionally substituted 4-6 membered heterocyclyl, optionally substituted phenyl, cyano, alkylaminoalkoxy, alkylaminoalkoxyalkoxy, nitro, and lower alkyl substituted with one or more $R^2$;

wherein $R^2$ is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein $R^3$ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl;

or a pharmaceutically acceptable derivative thereof.

26. A compound of claim 25 wherein $R^1$ is a substituted or unsubstituted ring selected from pyrazol-5-yl, 2-oxo-1,2-dihydroquinol-7-yl, 1-oxo-1,2,3,4-tetrahydro-isoquinolyl, 2,3-dihydro-1,1-dioxo-benzo[d]isothiazolyl, benzothiazolyl, 2,3-dihydro-1H-indolyl, 2,3-dihydro-benzofuryl, 1,2,3,4-tetrahydro-isoquinolyl, quinolyl, isoquinolyl, 1,2,3,4-tetrahydroquinolyl and 5,6,7-trihydro-1,2,4-triazolo[3,4-a]isoquinolyl; wherein substituted $R^1$ is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholinylmethyl, methylpiperazinylmethyl, isopropylpiperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-aminoethyl, 1-(N-isopropylamino)ethyl, 2-(N-isopropylamino)ethyl, dimethylaminopropyl, dimethylaminoethoxy, 4- chlorophenoxy, phenyloxy, 1-methylpiperidin-4-yloxy, piperidin-4-yloxy, piperidinylethoxy, morpholinylethyloxy, 4-methylpiperazinylethoxy, 4-isopropylpiperazinylethoxy, piperidin-4-methoxy, 4-methylpiperidin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylamino)pyrrolidin-1-ylethoxy, isopropoxy, methoxy and ethoxy; or a pharmaceutically acceptable derivative thereof.

27. A compound of claim 26 wherein $R^1$ is substituted with 1-3 substituents independently selected from chloro, fluoro, amino, aminoethyl, hydroxy, methyl, ethyl, propyl, isopropyl, butyl, tert-butyl, sec-butyl, trifluoromethyl, pentafluoroethyl, nonafluorobutyl, 1,1-di (trifluoromethyl)-1-hydroxymethyl, methylcarbonyl, trifluoromethoxy, 1-methylpiperidin-4-yloxy, piperidin-4-yloxy, piperidinylethoxy, morpholinylethyloxy, 4-methylpiperazinylethoxy, 4-isopropylpiperazinylethoxy, piperidin-4-methoxy, 4-methylpiperidin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylamino)pyrrolidin-1-ylethoxy, isopropoxy, methoxy and ethoxy; or a pharmaceutically acceptable derivative thereof.

28. A compound of claim 22 wherein $R^1$ is selected from 3-trifluoromethylphenylmethyl, 3-trifluoromethylphenylethyl, 3-methoxyphenylmethyl, phenylethyl, 4-methoxyphenylethyl, 3,4-dimethoxyphenylethyl, 4-methylphenylethyl, 2-fluorophenylethyl, 3-fluorophenylethyl, 2-chiorophenylethyl, 4-chlorophenylethyl, 3,4-dichlorophenylethyl, and 3,5-dichlorophenylethyl; or a pharmaceutically acceptable derivative thereof.

29. A compound of claim 22 wherein $R^7$ is selected from substituted or unsubstituted 6 membered nitrogen containing heteroaryl, where substituted $R^7$ is substituted with one or more substituents selected from halo, —$OR^3$, —$SR^3$, —$SO_2R^3$, —$CO_2R^3$, —$C(O)NR^3R^3$, —$C(O)R^3$, —$NR^3R^3$, —$SO_2NR^3R^3$, —$NR^3C(O)OR^3$, —$NR^3C(O)R^3$, optionally substituted 3-6 membered heterocyclyl, optionally substituted phenyl, alkylaminoalkoxyalkoxy, nitro, cyano, oxo, lower alkyl substituted with one or more $R^2$; wherein $R^2$ is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and wherein $R^3$ is independently selected from H, $C_{1-4}$-alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl;

or a pharmaceutically acceptable derivative thereof.

30. A compound of claim 29 wherein $R^7$ is selected from 4-pyridyl, 4-pyrimidinyl, 5-pyrimidinyl, 6-pyrimidinyl, 4-pyridazinyl and 6-pyridazinyl; or a pharmaceutically acceptable derivative thereof.

31. A compound of claim 22 wherein $R^7$ is selected from substituted or unsubstituted 9-10 membered nitrogen containing heteroaryl, where substituted $R^7$ is substituted with one or more substituents selected from halo, —$OR^3$, —$SR^3$, —$SO_2R^3$, —$CO_2R^3$, —$C(O)NR^3R^3$, —$C(O)R^3$, —$NR^3R^3$, —$SO_2NR^3R^3$, —$NR^3C(O)OR^3$, —$NR^3C(O)R^3$, Boc, optionally substituted 3-9 membered heterocyclyl, optionally substituted phenyl, alkylaminoalkoxyalkoxy, nitro, cyano, oxo, lower alkyl substituted with one or more $R^2$;
  wherein $R^2$ is selected from H, fluoro, hydroxy, amino, $C_{1-3}$-alkylamino, $C_{1-3}$-dialkylamino, optionally substituted phenyl, and 4-6 membered heterocyclyl selected from morpholinyl, piperazin-4-yl, 1-methylpiperazin-4-yl, piperidin-1-yl, 1-methylpiperidin-4-yl, 1-Boc-piperidin-4-yl, pyrrolidin-1-yl, pyrrolidin-2-yl, and 1-Boc-pyrrolidin-2-yl; and
  wherein $R^3$ is independently selected from H, $C_{1-4}$- alkyl, $C_{1-2}$-fluoroalkyl, optionally substituted phenyl, optionally substituted 3-6 membered heterocyclyl selected from morpholinyl, piperazin-4-yl, and piperidin-4-yl, optionally substituted phenylmethyl, optionally substituted 3-6 membered heterocyclyl-$C_{1-2}$-alkyl wherein the heterocylyl ring is selected from selected from azetidin-3-yl, pyrrol-2-yl, pyrrol-1-yl, piperidin-4-yl and piperazin-4-yl;
  or a pharmaceutically acceptable derivative thereof.

32. A compound of claim 31 wherein $R^7$ is selected from 5-indazolyl, 4-quinolinyl, 6-quinolinyl, pyrrolo[2,3-b]pyridin-4-yl, pyrrolo[2,3-b]pyridin-3-yl, 5-isoquinolinyl and 4-quinazolinyl; or a pharmaceutically acceptable derivative thereof.

33. A compound of claim 22 wherein $R^1$ is selected from 4-tertbutylphenyl, 3,3-dimethyl-2,3-dihydroindolyl, 1-acetyl-3,3-dimethyl-2,3-dihydroindolyl, 3-tert-butylpyrazol-5-yl, 4,4-dimethyl-1,2,3,4-tetrahydroisoquinolin-7-yl, 4,4-dimethyl-2-(3-pyrrolo[2,3-b]pyridinyl)-1,2,3,4-tetrahydroisoquinolin-7-yl, and 4,4-dimethyl-2-(Boc)-1,2,3,4-tetrahydroisoquinolin-7-yl; and wherein $R^7$ is selected from 6-quinolinyl, pyrrolo[2,3-b]pyridin-3-yl, 4-pyridyl and 3-aminopyrid-4-yl; or a pharmaceutically acceptable derivative thereof.

34. A compound of claim 1 or a pharmaceutically acceptable salt thereof selected from 2-(4-(1,1-dimethylethyl)phenyl)-8-((4-pyridinylmethyl)amino)-3,4-dihydro-1(2H)-isoquinolinone.

35. A pharmaceutical composition comprising a pharmaceutically-acceptable carrier and a compound as in any of claims 1-33.

36. A method of treating angiogenesis in a subject, said method comprising administering an effective amount of a compound of claim 1.

37. A method of reducing blood flow in a tumor in a subject, said method comprising administering an effective amount of a compound of claim 1.

38. A method of reducing tumor size in a subject, said method comprising administering an effective amount of a compound of claim 1.

39. A method of treating diabetic retinopathy in a subject, said method comprising administering an effective amount of a compound of claim 1.

\* \* \* \* \*